United States Patent
Hauenstein et al.

(10) Patent No.: US 10,314,520 B2
(45) Date of Patent: Jun. 11, 2019

(54) SYSTEM AND METHOD FOR CHARACTERIZING BIOMECHANICAL ACTIVITY

(71) Applicant: SEISMIC HOLDINGS, INC., Menlo Park, CA (US)

(72) Inventors: Andreas Martin Hauenstein, San Mateo, CA (US); Ray Franklin Cowan, Mountain View, CA (US); Andrew Robert Chang, Sunnyvale, CA (US)

(73) Assignee: SEISMIC HOLDINGS, INC., Menlo Park, CA (US)

( * ) Notice: Subject to any disclaimer, the term of this patent is extended or adjusted under 35 U.S.C. 154(b) by 198 days.

(21) Appl. No.: 15/282,998

(22) Filed: Sep. 30, 2016

(65) Prior Publication Data

US 2017/0095181 A1 Apr. 6, 2017

Related U.S. Application Data

(60) Provisional application No. 62/236,425, filed on Oct. 2, 2015, provisional application No. 62/271,292, filed on Dec. 27, 2015.

(51) Int. Cl.
*A61B 5/11* (2006.01)
*A61B 5/00* (2006.01)
(Continued)

(52) U.S. Cl.
CPC .......... *A61B 5/1118* (2013.01); *A61B 5/1121* (2013.01); *A61B 5/6823* (2013.01);
(Continued)

(58) Field of Classification Search
CPC ......... A61B 5/1116; A61B 5/742; A61B 5/68; A61B 5/6802–5/6813; A61B 5/1114;
(Continued)

(56) References Cited

U.S. PATENT DOCUMENTS

| 4,633,094 A | 12/1986 | Knudsen |
| 5,143,088 A | 9/1992 | Marras et al. |

(Continued)

FOREIGN PATENT DOCUMENTS

| WO | 2011064705 A1 | 6/2011 |
| WO | 2011133799 A1 | 10/2011 |

(Continued)

OTHER PUBLICATIONS

Clifford, Michelle and Gomez, Leticia (2005), "Measuring Tilt with Low-g Accelerometers", in Freescale Semiconductor Application Note, (accessible at http://www.freescale.com/files/sensors/doc/app_note/AN3107.pdf), pp. 01-08.

(Continued)

*Primary Examiner* — Robert R Raevis
(74) *Attorney, Agent, or Firm* — Van Court & Aldridge LLP

(57) ABSTRACT

A system and method for collecting a set of kinematic data streams from an activity tracking system with at least one activity monitoring system that is attached to a user; segmenting at least a subset of the kinematic data streams into a set of segments according to actions of the user; generating a set of biomechanical signals from the kinematic data streams wherein a biomechanical signal characterize a biomechanical property during a segment and includes generating a first integration data set through data integration and baseline error correction across the set of segments of the normalized kinematic data stream and determining at least a first biomechanical signal that is at least partially based on the first integration data set; and applying the set of biomechanical signals.

17 Claims, 23 Drawing Sheets

(51) Int. Cl.
*G01C 21/16* (2006.01)
*G01C 22/00* (2006.01)

(52) U.S. Cl.
CPC ............ *G01C 21/16* (2013.01); *G01C 22/006* (2013.01); *A61B 5/6828* (2013.01); *A61B 5/742* (2013.01)

(58) Field of Classification Search
CPC ..... A61B 5/1118; A61B 5/112; A61B 5/1123; A61B 5/1126; A61B 5/1121; A61B 5/6823; A61B 5/6828; A61B 5/6801; G01C 21/16
USPC .......... 73/1.75, 1.77, 1.79, 1.81, 493, 865.4; 702/33, 85, 87, 2, 94, 95, 97, 104, 127, 702/141, 150, 151, 179, 180, 189; 600/587, 589
See application file for complete search history.

(56) References Cited

U.S. PATENT DOCUMENTS

| | | | |
|---|---|---|---|
| 5,158,089 A | 10/1992 | Swezey et al. | |
| 5,388,591 A | 2/1995 | Luca et al. | |
| 5,398,697 A | 3/1995 | Spielman | |
| 5,749,838 A | 5/1998 | Kline | |
| 5,916,181 A | 6/1999 | Socci et al. | |
| 5,919,149 A | 7/1999 | Allum | |
| 6,032,530 A | 3/2000 | Hock | |
| 7,264,554 B2 | 9/2007 | Bentley | |
| 7,431,703 B2 | 10/2008 | Salvi et al. | |
| 7,602,301 B1 | 10/2009 | Stirling et al. | |
| 7,634,379 B2 | 12/2009 | Noble | |
| 7,698,830 B2 | 4/2010 | Townsend et al. | |
| 8,206,325 B1 | 6/2012 | Najafi et al. | |
| 8,408,041 B2 | 4/2013 | Ten Kate et al. | |
| 8,749,391 B2 | 6/2014 | Flinsenberg et al. | |
| 8,773,256 B2 | 7/2014 | Ten et al. | |
| 8,924,248 B2 | 12/2014 | Tropper et al. | |
| 8,928,484 B2 | 1/2015 | Chang et al. | |
| 9,011,352 B2 | 4/2015 | Ten Kate et al. | |
| 9,128,521 B2 | 9/2015 | Chang et al. | |
| 9,286,782 B2 | 3/2016 | Chang et al. | |
| 9,706,962 B1* | 7/2017 | Uehara ................ A61B 5/7267 |
| 2003/0050546 A1 | 3/2003 | Desai et al. | |
| 2003/0181832 A1 | 9/2003 | Carnahan et al. | |
| 2004/0015103 A1 | 1/2004 | Aminian et al. | |
| 2005/0126026 A1 | 6/2005 | Townsend et al. | |
| 2007/0015611 A1 | 1/2007 | Noble et al. | |
| 2007/0062279 A1 | 3/2007 | Chan et al. | |
| 2007/0115277 A1 | 5/2007 | Wang et al. | |
| 2007/0118056 A1 | 5/2007 | Wang et al. | |
| 2007/0167671 A1 | 7/2007 | Miller | |
| 2008/0288026 A1 | 11/2008 | Cross et al. | |
| 2008/0319352 A1 | 12/2008 | Chow et al. | |
| 2009/0069722 A1 | 3/2009 | Flaction et al. | |
| 2009/0076419 A1 | 3/2009 | Namineni et al. | |
| 2009/0312973 A1 | 12/2009 | Hatlestad et al. | |
| 2010/0152622 A1 | 6/2010 | Teulings | |
| 2010/0205541 A1 | 8/2010 | Rapaport et al. | |
| 2010/0211349 A1 | 8/2010 | Flaction et al. | |
| 2010/0298655 A1 | 11/2010 | McCombie et al. | |
| 2010/0312152 A1 | 12/2010 | Sarkodie-Gyan et al. | |
| 2010/0317489 A1 | 12/2010 | Flaction | |
| 2011/0063114 A1 | 3/2011 | Ikoyan | |
| 2011/0172951 A1 | 7/2011 | Schlumbohm | |
| 2011/0207581 A1 | 8/2011 | Flaction | |
| 2011/0264325 A1 | 10/2011 | McLaughlin et al. | |
| 2012/0016624 A1 | 1/2012 | Caritu et al. | |
| 2012/0053890 A1 | 3/2012 | Acht et al. | |
| 2013/0015976 A1 | 1/2013 | Chang et al. | |
| 2013/0084805 A1 | 4/2013 | Pasquero et al. | |
| 2013/0158365 A1 | 6/2013 | Chey et al. | |
| 2013/0190657 A1 | 7/2013 | Flaction et al. | |
| 2013/0190658 A1 | 7/2013 | Flaction et al. | |
| 2013/0207889 A1 | 8/2013 | Chang et al. | |
| 2014/0228985 A1 | 8/2014 | Elliott et al. | |
| 2014/0244009 A1 | 8/2014 | Mestas et al. | |
| 2014/0270387 A1 | 9/2014 | Hoof et al. | |
| 2014/0277633 A1 | 9/2014 | Flaction | |
| 2014/0364769 A1 | 12/2014 | Chang et al. | |
| 2015/0040669 A1 | 2/2015 | Borkholder et al. | |
| 2015/0100141 A1 | 4/2015 | Hughes | |
| 2015/0228118 A1 | 8/2015 | Eade et al. | |
| 2015/0272483 A1* | 10/2015 | Etemad ................ A61B 5/0488 600/409 |
| 2016/0014826 A1 | 1/2016 | Mizikovsky et al. | |
| 2016/0042529 A1 | 2/2016 | Tao et al. | |
| 2016/0051858 A1 | 2/2016 | Flaction et al. | |
| 2016/0128619 A1 | 5/2016 | Geller et al. | |
| 2017/0027803 A1* | 2/2017 | Agrawal ............... A61B 5/6828 |
| 2017/0095181 A1 | 4/2017 | Hauenstein et al. | |
| 2017/0095692 A1 | 4/2017 | Chang et al. | |
| 2017/0095693 A1 | 4/2017 | Chang et al. | |
| 2017/0182360 A1 | 6/2017 | Chang et al. | |
| 2017/0188894 A1 | 7/2017 | Chang et al. | |
| 2017/0258374 A1 | 9/2017 | Ly et al. | |
| 2017/0273601 A1 | 9/2017 | Wang et al. | |
| 2017/0344919 A1 | 11/2017 | Chang et al. | |

FOREIGN PATENT DOCUMENTS

| | | |
|---|---|---|
| WO | 2013024461 A1 | 2/2013 |
| WO | 2015069124 A1 | 5/2015 |

OTHER PUBLICATIONS

Unknown, "Accelerometer", in Wikipedia (archived Apr. 1, 2011 at http:i/web archive.org/V\leb/2011 0401205940/http://en.wikipedia.org/wiki/Accelerometer), pp. 1-21.

Unknown, "Back Pain", in Wikipedia (archived Feb. 25, 2011 at http:l/web.archive.org/web/20110225132'125/ 0http://en.wikipedia.orgiwiki/Back~pain).. pp. 1-22.

Unknown, "Mahalanobis Distance", in Wikipedia (ardlived Mar. 29, 2010 at http://web.archive.orf!/ 0 webi20130329232341/http://len_wikipedia.org_l'<>viki/Mahalanobis_distance), pp. 1-8.

Unknown, "Rotation", in Wikipedia (archived Mar. 31, 2011 at http://web archive.org/web/20110331232736/http://en.wikipedia.org/wiki/Rotation), pp. 1-13.

Unknown, "Sensors", at freescale.com (accessed May 14, 2012 at http://www.freescale.com/webapp/sps/site/homepage.jsp?nodel=011269). pp. 1-2.

Unknown, "Neutral Spine", in Wikipedia (archived Feb. 12, 2011 at http://web.archive.org/web/20110212145135/http://en.wikipedia.orglwiki/Neutral_spine), pp. 1-7.

Kesson, Malcolm, "Mel. Align Y Axis to Vector", in CG References & Tutorials at Fundza.com (accessible at http://www.fundza.com/mel/axis_to_vector/index.html), pp. 1-6, Jun. 1, 2002.

Patel, A.T. and Ogle, Abna A., "Diagnosis and Management of Acute Low Back Pain", in American Family Physician 15:61 {6) (accessible at http://aafp.org/afp/2000/0315/p1779.html), pp. 1779-1786, Mar. 15, 2000.

Unknown, "Information from Your Family Doctor Acute Low Back Pain", in American Family Physician 15 51 (6) (accessible at http://www.aafp.org/afp/2000/0315/p1789 html), pp. 1-4, Mar. 15, 2000.

Unknown, "A Patient's Guide to Rehabilitation for Low Back Pain", University of Maryland Spine Program (archived 8 Jun. 7, 2011 at http://web.archive.org/web/20110607181952/http://www.umm.edu/spinecenter/education/rehabilitation_for_low_back_pain.htm). pp. 1-10, Jun. 19, 2008.

* cited by examiner

SYSTEM AND METHOD FOR CHARACTERIZING BIOMECHANICAL ACTIVITY

CROSS-REFERENCE TO RELATED APPLICATIONS

This Application claims the benefit of U.S. Provisional Application No. 62/236,425, filed on 2 Oct. 2015, and U.S. Provisional Application No. 62/271,292, filed on 27 Dec. 2015, both of which are incorporated in their entireties by this reference.

TECHNICAL FIELD

This invention relates generally to the field of biomechanical sensing, and more specifically to a new and useful system and method for characterizing biomechanical activity.

BACKGROUND

In recent years, numerous fitness monitoring apps and devices have been introduced to the public. Many of these devices function as basic pedometers, or step counters. Other devices characterize activity in a generic manner to quantify activity in an abstract manner. Such tools, however, fail to provide insight into particular performance metrics for a participant. Biomechanical tools, such as motion capture, can be used to provide detailed information on the involved mechanics of a participant. However, such tools often require complicated setups and may be restricted to a laboratory or other controlled environment, and detailed biomechanical analysis is limited to individuals with access to such research setups. Thus, there is a need in the biomechanical field to create a new and useful system and method for characterizing biomechanical activity. This invention provides such a new and useful system and method.

DESCRIPTION OF THE EMBODIMENTS

The following description of the embodiments of the invention is not intended to limit the invention to these embodiments but rather to enable a person skilled in the art to make and use this invention.

1. Overview

Figure 1:
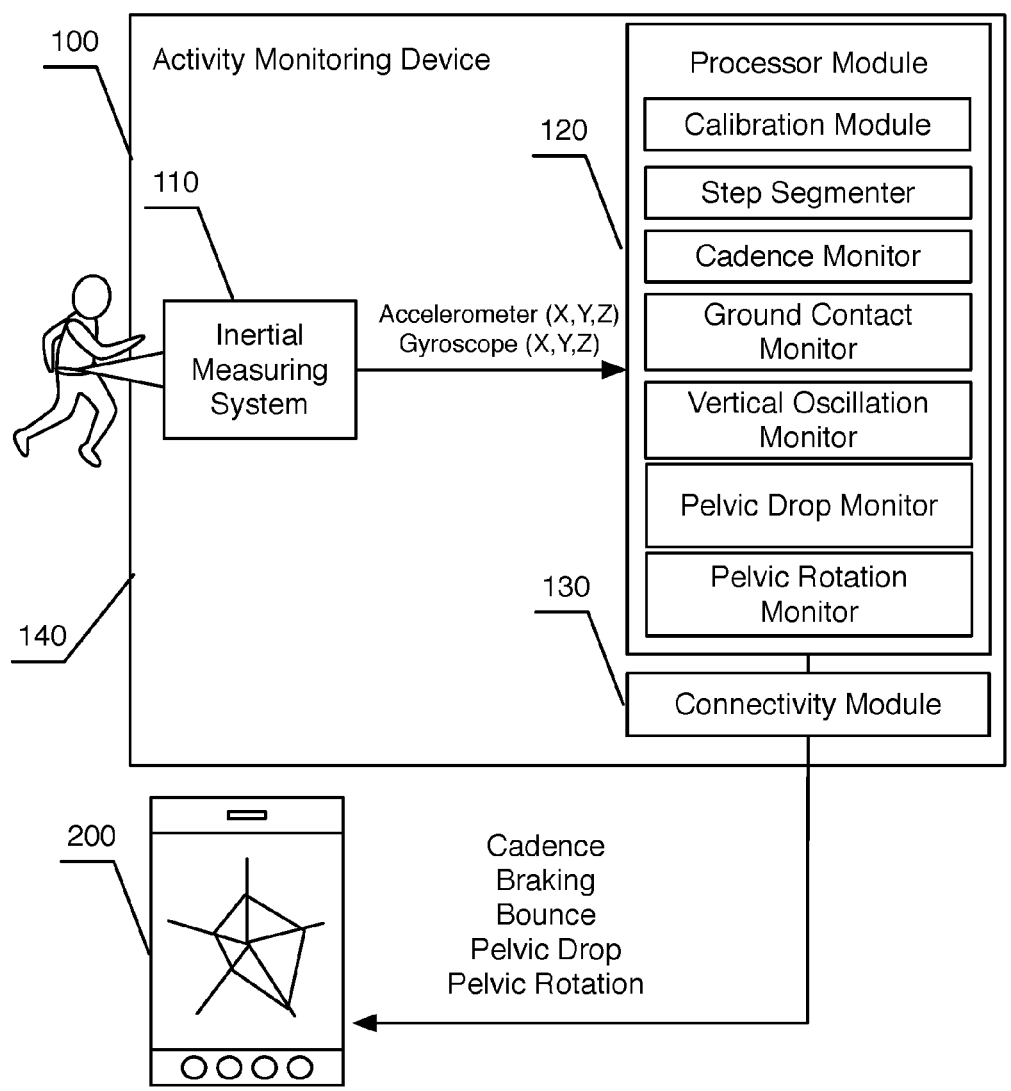
FIG. 1 is a schematic representation of a system of a preferred embodiment.

As shown in FIG. 1, a system and method of a preferred embodiment involves the transformation of collected data from an inertial measurement unit into a set of biomechanical signals. The system and method function to use kinematic sensor data in generating a detailed biomechanical characterization of motion properties. The biomechanical characterizations of motion properties are preferably manifested through a set of biomechanical signals, which can be used in generating a report, triggering a system response, or producing any suitable tangible result.

A biomechanical signal preferably parameterizes a biomechanical-based property of some action by a user. More particularly, a biomechanical signal quantifies at least one aspect of motion that occurs once or repeatedly during a task. For example, in the case of walking or running, how a participant takes each step can be broken into several biomechanical signals. In a preferred implementation, the system and method preferably operate with a set of biomechanical signals that includes ground contact time, braking, pelvic rotation, pelvic tilt, pelvic drop, vertical oscillation of the pelvis, forward oscillation, forward velocity properties of the pelvis, step duration, stride or step length, step impact or shock, and/or foot pronation. Additionally, the biomechanical signals can include left/right foot detection, which may be applied for further categorizing or segmenting of biomechanical signals according to the current step side. The pelvis is used as a preferred reference point for a wide variety of activities, including running. The pelvis can have a strong correlation to lower body movements and can be more isolated from upper body movements such as turning of the head and swinging of the arms. The sensing point is preferably centrally positioned near the median plane in the trunk portion of the body. Additional sensing points or alternative sensing points may be used. In one variation, the position and/or number of sensing points can be adjusted depending on the activity.

The set of biomechanical signals may form a primitive set of signals from which a wide variety of activities can be monitored and analyzed. For example, the system and method may be applied to activity use-cases such as gait-analysis, walking, running, lifting, swimming, skiing, skating, biking, rowing, golfing, baseball, basketball, bowling, soccer, football, dancing/choreography, ballet and/or any suitable activity. The activity is preferably characterized by predictable, repetitive, or predefined movements. Some activities may include additional or alternative biomechanical signals in the primitive set of biomechanical signals. Additionally, a system of a preferred embodiment can include alternative and/or additional sensing points, which can be used for generating or refining alternative and/or additional biomechanical signals.

A biomechanical signal can be a function of time. The biomechanical signal can additionally be a real-time signal, wherein each data point is a value that corresponds to some instance of time. The real-time value can be a current value for the biomechanical property or a running average. For example, real-time step time can be averaged over a window spanning a defined set of steps (e.g., 4 steps). An averaging window may be equally weighted or weighted. In one variation, the averaging window is dynamically adjusted. The averaging window can be adaptively increased or decreased according to the activity type, the state of the activity, the biomechanical signals of a user, the operating conditions of the system (e.g., power and/or communication properties). In one exemplary operating mode, the averaging window may be adaptively increased if the biomechanical signals of a user are consistent and within a target range, which functions to minimize communication and power consumption of an activity monitoring device while providing less resolution of the biomechanical signals during times of lower variability. In another exemplary operating mode, the averaging window may be adaptively decreased if the biomechanical signals are not within a target range or have varied outside of normal performance, which functions to provide more resolution on their biomechanical performance. In yet another exemplary operating mode, the averaging window may be adjusted based on whether the activity is a sprint, a regular mile run (e.g., step duration), or a longer distance run. Averaging, smoothing, and other error correcting or filtering processes may be applied to a real-time signal.

The system and method in one preferred embodiment function to leverage the kinematic sensor data of a single sensing region. Sensing in a single region can simplify the setup of the system and the cost of the system. In one exemplary implementation, the system and method may be used within a wearable activity-tracking device. A sensor can be attached or otherwise positioned along the waist region of a participant user (e.g., the lumbar or sacral region of the back). Various use-cases could be built on top of such a system including biomechanical diagnostic tools, biofeedback tools, gait-analysis tools, rehabilitation and physical therapy tools, coaching tools, injury prevention monitoring, performance monitoring applications, reactive sports equipment, and other suitable products. Additionally, the system may be extended to multiple point sensing. Multiple points of sensing can function to expand the number, accuracy, and variety of biomechanical signals.

As shown in FIG. 1, a system of a preferred embodiment can include an inertial measuring system 110, a signal processor module 120, connectivity module 130, and a user application 200. In one preferred implementation, the inertial measuring system is integrated with an activity monitoring device 100 that includes the inertial measurement device 110, a housing 140, the signal processor module 120, memory/storage, and a communication component. The activity monitoring device 100 can additionally include any suitable components to support computational operation such as a processor, RAM, a flash memory, user input elements (e.g., buttons, switches, capacitive sensors, touch screens, and the like), user output elements (e.g., status indicator lights, graphical display, speaker, audio jack, vibrational motor, and the like), communication components (e.g., Bluetooth LE, Zigbee, NFC, Wi-Fi, and the like), and/or other suitable components.

Figure 2A:
FIGS. 2A-2G are schematic representations of exemplary single and multi point sensing configurations.

In one variation, the system includes a single activity monitoring device 100. One preferred embodiment uses a single unit activity monitoring device 100 that senses at a single point. The activity monitoring device 100 is preferably positioned in the waist region, and more specifically, the activity monitoring device can be positioned along the back in the lumbar or sacral region as shown in FIG. 2A. A single activity monitoring device 100 can be used, for example, in left and right foot detection, stride or step analysis, braking analysis. The single point of sensing from the activity monitoring device can be positioned at any suitable alternative position.

Figure 2B:
Figure 2C:
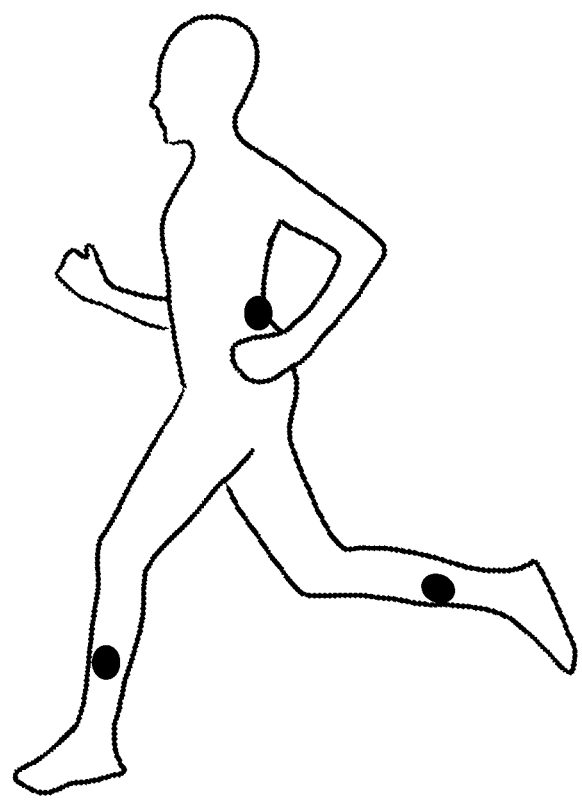
Figure 2D:
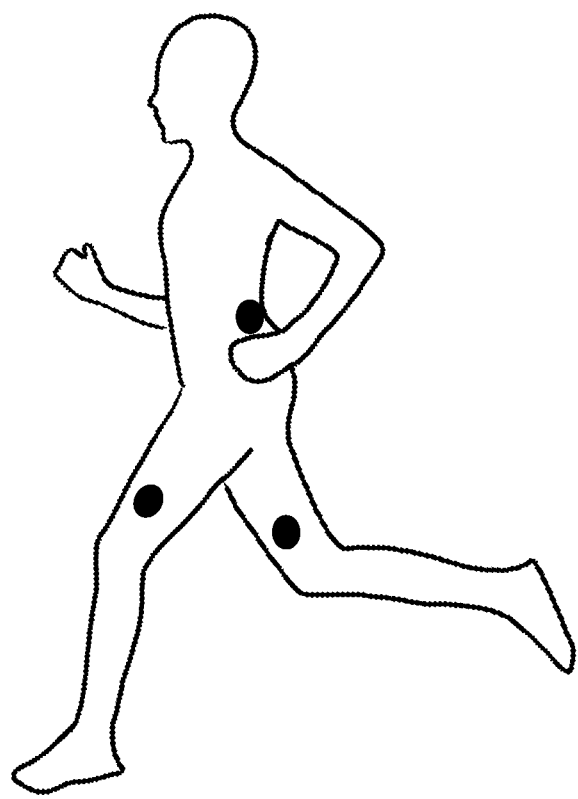
Figure 2E:
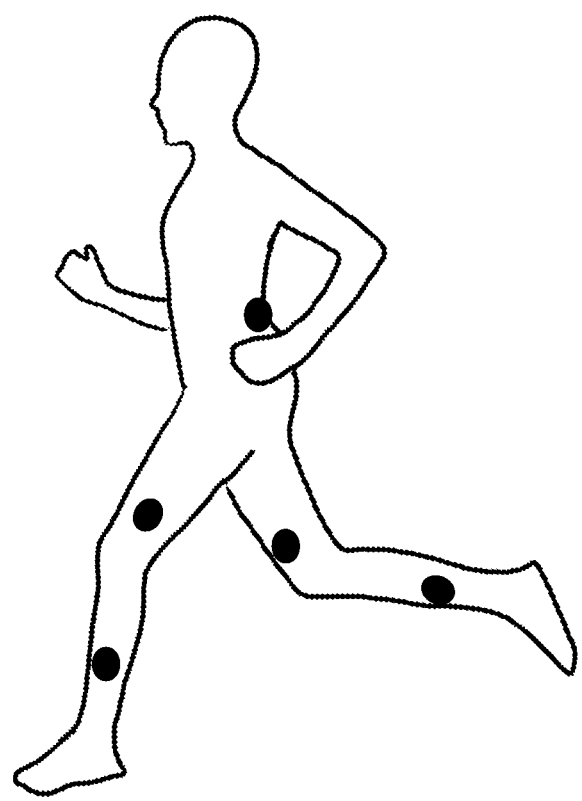
Figure 2F:
Figure 2G:
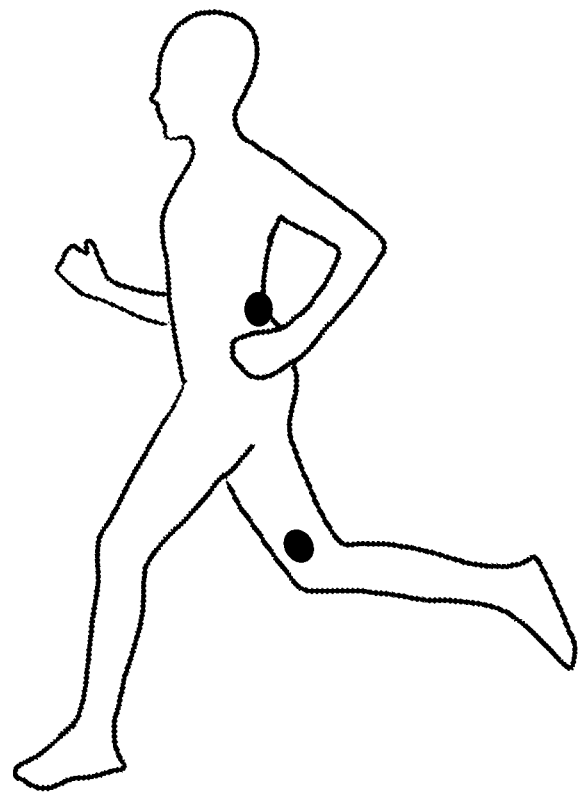
Figure 3:
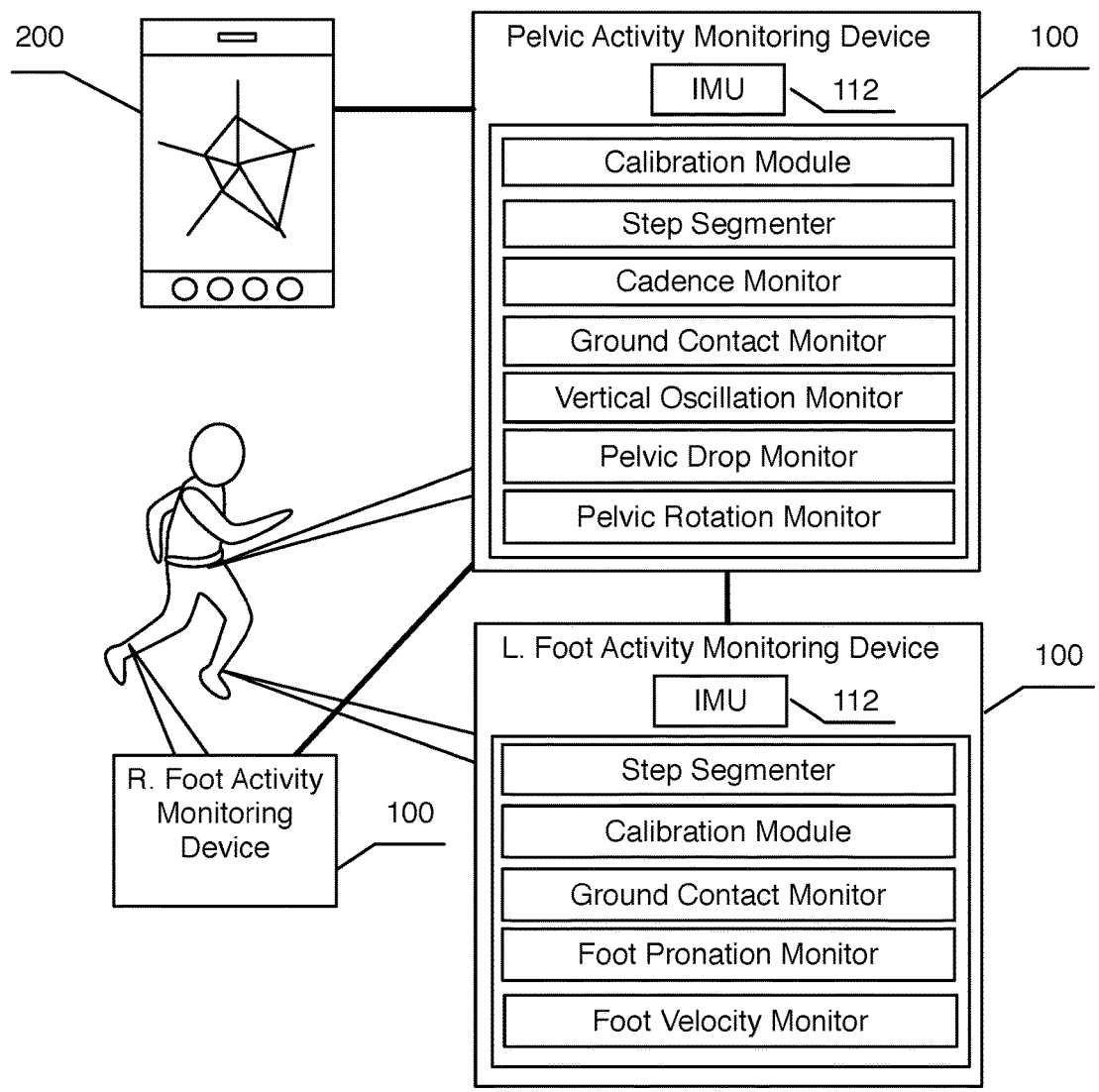
FIG. 3 is a schematic representation of a system of a multi-point system utilizing two activity monitoring devices.

In another variation, the activity monitoring device 100 uses a multi-point sensing system as shown in FIG. 3, wherein a set of inertial measurement systems 112 measure motion at multiple points. The points of measurement are preferably communicated to one or more master activity monitoring devices 110. As shown in FIG. 3, distinct activity monitoring devices may act in cooperation. Alternatively, distinct, independent activity monitoring devices 110 may each communicate with a user application 200 or other remote computing resource. Alternatively, one activity monitoring device may connect to multiple IMUs at distinct points. The points of measurement may be in the waist region, the upper leg, the lower leg, the foot, and/or any suitable location. Other points of measurement can include the upper body, the head, or portions of the arms. Various configurations of multi-point sensing can be used for sensing biomechanical signals. Different configurations may offer increased resolution, more robust sensing of one or more signals, and for detection of additional or alternative biomechanical signals. A foot activity monitoring device could be attached to or embedded in a shoe. A shank or thigh activity monitoring device could be strapped to the leg, embedded in an article of clothing, or positioned with any suitable approach. In one preferred variation of multi-point sensing, the system includes a pelvic activity monitoring device and a right and left lower leg activity monitoring device. The right and left lower leg activity monitoring device may be coupled to the foot as shown in FIG. 2B or the shank of each of the legs as shown in FIG. 2C. The lower leg activity monitoring device can provide additional kinematic insights into how the extremities of the leg are moving. In another variation, the system can include activity monitoring devices on the right and left thigh as shown in FIG. 2D. The thigh activity monitoring devices can be used in combination (as shown in FIG. 2E) or as an alternative to the lower leg activity monitoring devices. The thigh activity monitoring devices can be used to give relative rotation and motion between the thigh and the foot area and/or between the thigh and the pelvic region. While multi-point sensing preferably uses symmetrical sensing for both legs, one alternative may use a single additional sensing point on the leg as shown in FIGS. 2F and 2G.

Multiple points of sensing can be used to obtain motion data that provides unique motion information that may be less prevalent or undetectable from just a single sensing point. Multiple points can be used in distinguishing between right and left leg actions. The multiple points can be used to obtain clearer signals for particular actions such as when the foot strikes the ground. Multiple points can additionally be used in providing relative kinematics between different points of the body. The relative angular orientation and displacement can be detected between the foot, thigh, and/or pelvic region. Similarly, relative velocities between a set of activity monitoring systems can be used to generate particular biomechanical signals.

The inertial measuring system 110 functions to measure multiple kinematic properties of an activity. The inertial measuring system 110 preferably includes at least one inertial measurement unit 112. An inertial measurement unit 112 can include at least one accelerometer, gyroscope, magnetometer, or other suitable inertial sensor. The inertial measurement unit 112 preferably includes a set of sensors aligned for detection of kinematic properties along three orthogonal axes. In one variation, the inertial measurement unit 112 is a 9-axis motion-tracking device that includes a 3-axis gyroscope, a 3-axis accelerometer, and a 3-axis magnetometer. The inertial measuring system 110 can additionally include an integrated processor that provides sensor fusion in hardware, which effectively provides a separation of forces or sensed dynamics for data from a sensor. The on-device sensor fusion may provide other suitable sensor conveniences. Alternatively, multiple distinct sensors can be combined to provide a set of kinematic measurements.

An inertial measuring system 112 can additionally include other sensors such as an altimeter, global positioning system (GPS), or any suitable sensor. Additionally, the activity monitoring device can include a communication channel to one or more computing devices with one or more sensors. For example, an inertial measuring system can include a Bluetooth communication channel to a smart phone, and the smart phone can track and retrieve data on geolocation, distance covered, elevation changes, and other data.

The signal processor module functions to transform sensor data generated by the inertial measuring system 112. As shown in FIG. 1, the signal processor module can include a step segmenter, a calibration module, a ground contact monitor, cadence monitor, vertical oscillation monitor, a pelvic rotation monitor, and a pelvic drop monitor, and/or any suitable biomechanical signal monitor which function to output a set of biomechanical signals. Additional or alternative biomechanical signals may be used. In a variation using multiple sensing points, the signal processor module for one of the activity monitoring devices can be customized for the particular sensing point. A signal processor module of a foot activity monitoring device can include a step segmenter, a calibration module, a ground contact monitor, a foot pronation module, and foot velocity module. A signal processor module of a thigh activity monitoring device can include a step segmenter, a calibration module, a thigh orientation monitor, and a thigh velocity monitor.

The various signal processor modules may use a single point activity monitoring device variation or a multi-point activity monitoring device variation. In the multi-point variation, different biomechanical signals may depend on different sets of sensing points—a first biomechanical signal may depend on a first set of sensing points, a second biomechanical signal may depend on a second set of sensing points. For example, a step segmenter may utilize kinematic data from a pelvic sensing point and a foot sensing point, while foot pronation may utilize a foot sensing point and a shin sensing point. Similarly, in a multiple sensing point variation, a first biomechanical signal may originate from kinematic data of a first sensing point (e.g., a pelvic sensing point used for pelvic tilt) and a second biomechanical signal originates from kinematic data of a second sensing point (e.g., a foot sensing point used for foot strike angle).

The signal processor module 120 is software operating on the output of the inertial measuring system 110. For example, a wearable device with a battery, a communication module, and some form of user control can generate the biomechanical signals on a single device. The signal processor module 120 may alternatively be application logic operable on a secondary device such as a smart phone. In this variation, the signal processor module can be integrated with the user application 200. In yet another variation, the signal processor module 120 can be remote processor accessible over the network. For example, biomechanical signals may be generated in the cloud, which functions to provide remote processing. Remote processing can enable large datasets to be more readily leveraged when analyzing kinematic data.

Figure 4:
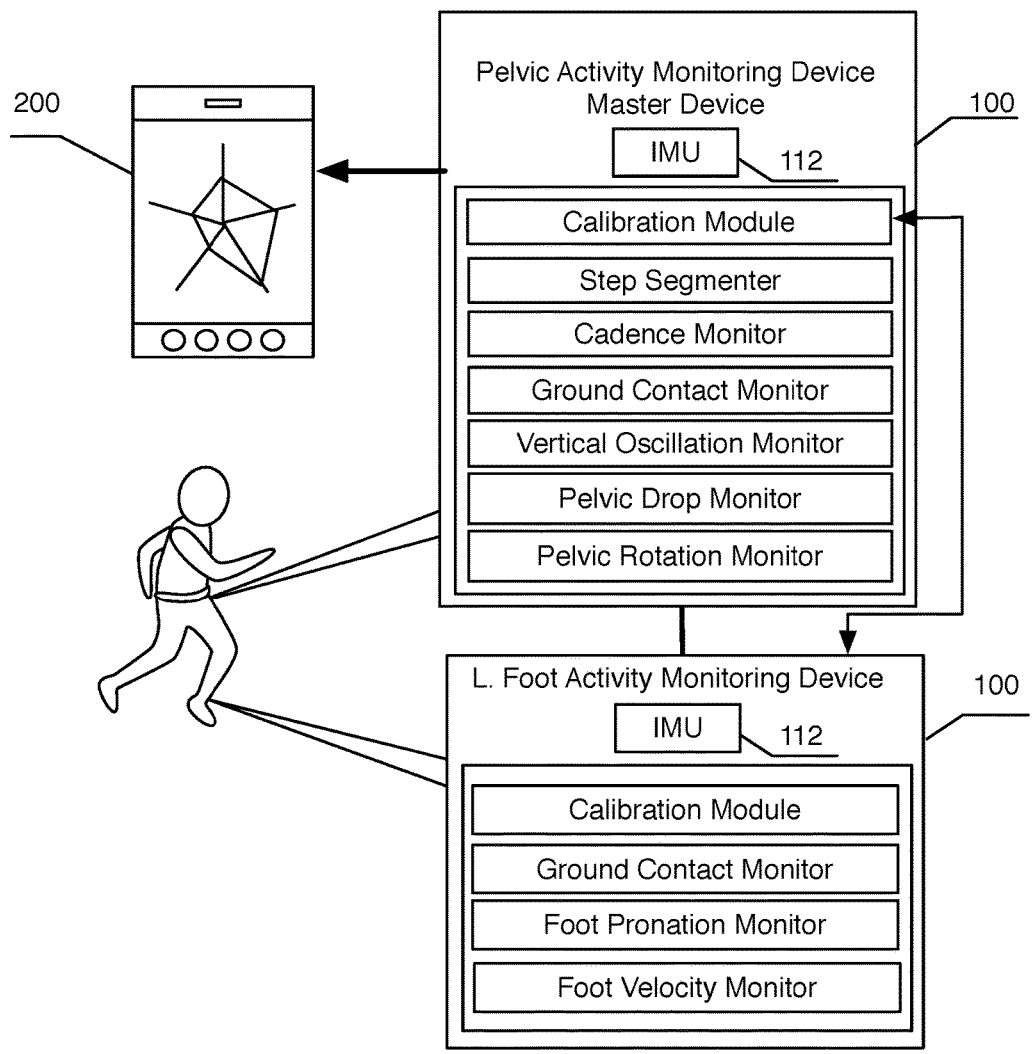
FIG. 4 is a schematic representation of a system of a multi-point system utilizing two activity monitoring devices with one master.

In a variation with multiple sensing points, a set of signal processor modules can be included in each activity monitoring device. The generation of the biomechanical signals can be completed on each of the activity monitoring devices. Alternatively, kinematic data, processed data, and/or a partial set of biomechanical signal data can be communicated between the set of activity monitoring devices such that data from multiple sensing points can be used in generating a biomechanical signal. As shown in FIG. 4, one variation can include a right foot and left foot activity monitoring device communicating with a parent pelvic activity monitoring device. The left and right activity monitoring devices can generate specific biomechanical signals. A subset of the biomechanical signals may be used by the parent activity monitor to generate an additional or alternative biomechanical signal. The parent pelvic activity monitoring device can communicate data to a user application on a user device. Alternatively, each of the activity monitoring devices may directly communicate with the user application. The user application can facilitate completion or generation of all or some biomechanical signals.

The user application 200 functions as at least one outlet of the biomechanical signal output. The user application 200 can be any suitable type of user interface component. Preferably, the user application 200 is a graphical user interface operable on a user computing device. The user computing device can be a smart phone, a desktop computer, a TV based computing device, a wearable computing device (e.g., a watch, glasses, etc.), or any suitable computing device. In one exemplary implementation, the user application 200 is used to visibly represent the biomechanical signals as a graphic that characterizes the biomechanical properties of a participant's performance.

The user application 200 can alternatively be a website accessed through a client browsing device. Alternatively, the biomechanical signals may be accessed synchronously or asynchronously through an application programming interface (API). In one variation, the user application 200 can be integrated with the inertial measuring system or part of a secondary device. For example, the device of the inertial measuring system may include a set of audio or visual outputs that can be used in representing the biomechanical signals. Haptic feedback elements and other forms of user feedback may additionally be controlled by the user application.

The system may additionally include elements to measure and report other metrics. Additional metrics can include activity-based metrics such as number of actions (e.g., steps, swings, etc.), distance, time, elevation change, speed, and other metrics corresponding to performing an activity. In another variation, the metrics can include biological metrics, which may correlate to biological functions other than the motion of the body such as heart-rate, blood-chemical levels, brain activity, body temperature, and other suitable biological functions.

2. Method

Figure 5:
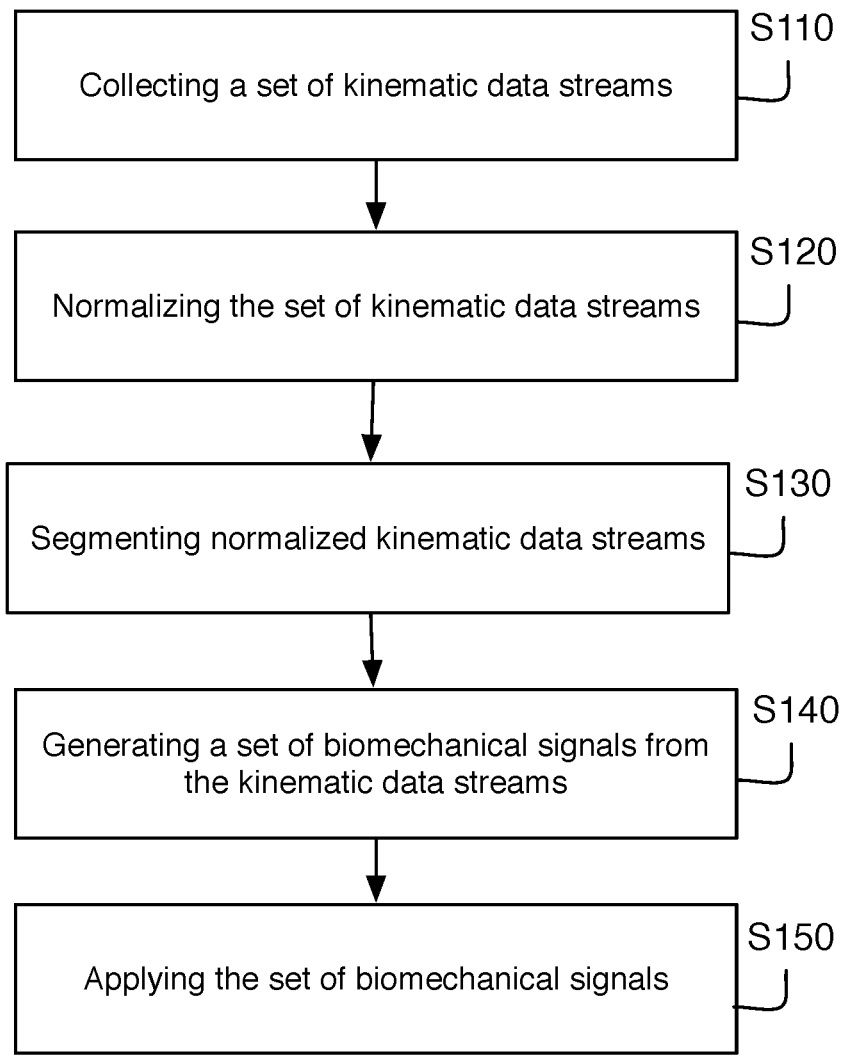
FIG. 5 is a flowchart representation of a method of a preferred embodiment.

As shown in FIG. 5, a method of a preferred embodiment can include collecting a set of kinematic data streams S110, normalizing the set of kinematic data streams S120, segmenting normalized kinematic data streams S130, generating a set of biomechanical signals from the kinematic data streams S140, and applying the set of biomechanical signals S150. As described above, the method can function to use kinematic sensor data in generating detailed biomechanical characterizations of body motion during some activity. The method can be applied to activities such as walking, running, lifting, swimming, skiing, skating, biking, rowing, golfing, and/or other suitable activities. One potential benefit of the method is that biomechanical signals can characterize discrete actions of some activity. The method preferably segments repetitive actions such as steps or strides when walking or running, pedal cycles when biking, rows when rowing, turns when skiing or snowboarding, or other repetitive actions. The method could similarly be applied to isolated discrete actions such as the swing in golfing or a lift during weight lifting.

Figure 6:
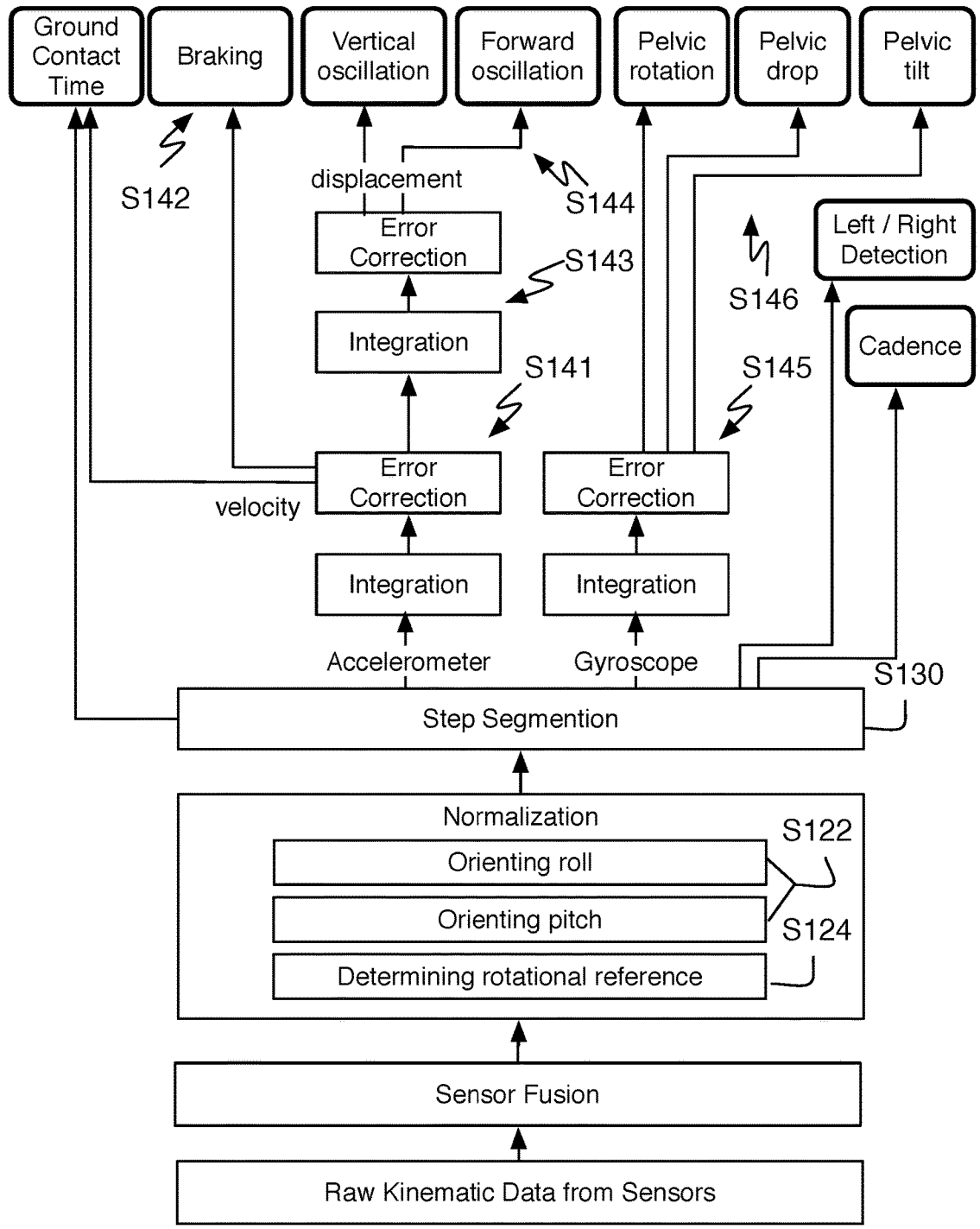
FIG. 6 is a detailed flowchart representation of a processing framework for an exemplary set of biomechanical signals.

The method is additionally applied to generating a set of multiple biomechanical signals. As shown in FIG. 6, the method may enable a suite of biomechanical signals to be generated from a kinematic data stream. In one running-focused implementation, the method can be used to generate biomechanical signals for ground contact time, braking, vertical oscillation, forward oscillation, pelvic rotation, pelvic drop, and pelvic tilt, cadence. Additionally, the method can be used for left/right foot detection, which can be used to provide biomechanical signals segmented by right and left steps.

The method is preferably implemented by a system as described above. Preferably, the method is implemented in association with at least one positioned inertial measuring system and more preferably at least one point inertial measuring system substantially coupled to the waist region of a participant. For example, a sensing device may be attached to the back portion of a waistband of a garment. Alternatively, the method can involve sensing kinematic data from multiple points, and applying that kinematic data to generating the set of biomechanical signals.

In one variation, the method is implemented on a stand-alone device connected with a sensing system. In another variation, the method is implemented on a native application operable on a personal computing device (e.g., smart phone, wearable computing device, or personal computer). In yet another variation, the method can be implemented in the cloud on a remote server. The method may alternatively be implemented through any suitable system.

Block S110, which includes collecting a set of kinematic data streams, functions to sense, detect, or otherwise obtain sensor data. In one variation, data of the kinematic data streams is raw, unprocessed sensor data as detected from a sensor device. Raw sensor data can be collected directly from the sensing device, but the raw sensor data may alternatively be collected from an intermediary data source. A sensing device is preferably an activity monitoring device with at least one inertial measurement unit as described above, but any suitable sensing system may be used. An intermediary data source could provide stored data collected from any suitable system. In another variation, the data can be pre-processed. For example, data can be filtered, error corrected, or otherwise transformed. In one variation, in-hardware sensor fusion is performed by an on-device processor of the inertial measurement unit. Sensor fusion can be a process for calibrating and/or orienting the kinematic data streams. Provided sensor fusion may be used in place of normalization process S120, but may alternatively be used in combination Any suitable pre-processing may additionally be applied to the data during the method.

The individual kinematic data streams preferably correspond to distinct kinematic measurements along a defined axis. The kinematic measurements are preferably along a set of orthonormal axes (e.g., an x, y, z coordinate system). As described below, the axis of measurements may not be aligned with a preferred or assumed coordinate system of the activity. Accordingly, the axis of measurement by one or more sensor(s) may be calibrated for analysis in block S120. One, two, or all three axes may share some or all features of the calibration, or be calibrated independently. The kinematic measurements can include acceleration, velocity, displacement, force, angular velocity, angular displacement, tilt/angle, and/or any suitable metric corresponding to a kinematic property or dynamic property of an activity. Preferably, a sensing device provides acceleration as detected by an accelerometer and angular velocity as detected by a gyroscope along three orthonormal axes. The set of kinematic data streams preferably includes acceleration in any orthonormal set of axes in three-dimensional space, herein denoted as x, y, z axes, and angular velocity about the x, y, and z axes. Additionally, the sensing device may detect a magnetic field through a three-axis magnetometer.

The sensor device is preferably attached to the user in a position that stays substantially stable on a user during an activity session. Preferably, the sensor device moves with the user as opposed to the clothing. However, biomechanical signal processes may account for clothing movement. The sensor device can be attached to the pelvic region or any suitable location. In some variations, multiple sensor devices of an activity monitoring system are attached in distinct locations such as the pelvic region and one or both feet. In a preferred implementation, the collecting of kinematic data streams S110 can be collected from an inconsistently mounted sensing device. A sensing device is generally characterized as inconsistently mounted when the orientation of a sensor is substantially not identical between different mountings and different users. The sensing device (e.g., the activity monitoring device) may be worn by a user using a clip or holder that attaches to the clothes, belt, or other article worn by a user. Alternatively, the sensor may be inserted or embedded in an article worn by a user. The sensor will generally have different orientations between uses and potentially during use. Block S120 of the method can preferably account for such variability in orientation changes.

Block S120, which includes normalizing the set of kinematic data streams, which functions to set a reference context in which the kinematic data is collected and analyzed. Normalizing can involve standardizing the kinematic data and calibrating the kinematic data to a coordinate system of the participant. The inertial measuring system is preferably part of a sensing device that can be attached or otherwise fixed into a certain position during an activity. The sensing device could be a dedicated sensing device such as a fitness tracker, but may alternatively be integrated into an article such as smart apparel integrated with an inertial measuring system. The sensing device may alternatively be a mobile device such as a smart phone, watch, or wearable where an inertial measuring system of that device can be leveraged by a user application. The position of the sensing device can be static during the activity but may also be perturbed and changed. Preferably, the inertial measuring system is positioned in the waist region and more specifically in the lumbar or sacral region of the back. Additional inertial measuring systems can be positioned at varying points to provide kinematic data streams for other portions of the body. The foot, the shank of the leg, and the thigh are three optional points. Inertial measuring systems can capture kinematic data streams for both the left and right leg.

Figure 7:
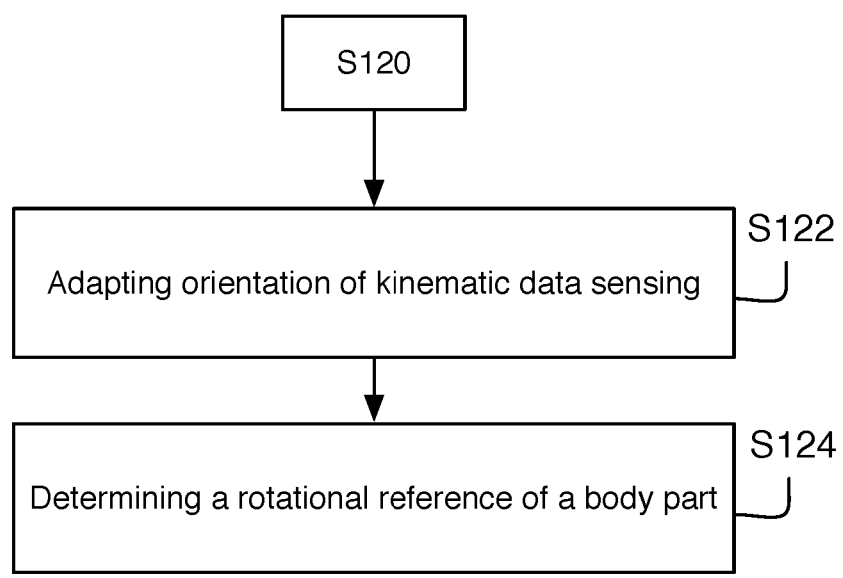
FIG. 7 is a flowchart representation of a variation for calibrating detection.

Because the inertial measuring system may be removable, the exact orientation of the device can vary between different instances of use and/or during an activity. The normalization is preferably performed as an initial process, but can additionally be performed periodically or continuously during an activity. In one variation, the method can include directing a participant in calibrating actions. For example, an application may direct a participant to start walking. The application can perform at least a subset of calibration during the walking. Once calibration is completed, the application can direct the participant to begin his or her running workout. Alternatively, the calibration can happen in the background. More preferably, the method may perform calibration in response to a participant performing some action without being prompted. For example, at least a portion of the calibration may be performed after a user begins walking or running. In one implementation, the yaw calibration is performed upon starting an activity session (such as a running session) within an application. GPS or other forms of motion sensing may be used to detect when a participant has moved a particular distance. In one variation, calibration can be retroactive after completion of an activity. Alternatively, calibrating and adapting orientation of the kinematic data streams can be achieved without calibrating to a participant's movements and may assume a forward-backwards direction or orientation and calibrate the pitch and roll of an activity monitoring device. The calibration of pitch, roll, and yaw could performed on all three, but in some cases, the orientation of an inertial measuring system may be biased to one of a limited set of orientations. Preferably, at least the forward-backward orientation is biased such that either one side or the other is facing forward. This binary forward-backward orientation may be simply determined. Alternatively, determining a forward-backward orientation may include calibrating a forward-backward orientation. Such a calibration process may utilize the bias towards particular expected orientations. The calibrating process preferably uses the kinematic data streams from a current session of activity. The calibrating process may additionally use calibrating information or kinematic data stream information from a previous activity session. In one variation, one ore more of the d As shown in FIG. 7, calibrating detection of the set of kinematic data streams can include adapting orientation of kinematic data sensing to how the activity monitoring device is affixed to a participant S122 and determining a rotational reference of a body part S124.

Block S122, which includes adapting orientation of kinematic data sensing to how the activity monitoring device is affixed to a participant, functions to convert the sensor orientation to a suitable coordinate system for analyzing the activity. Block S122 provides flexibility in the restrictions in how a sensing device is attached to a participant. Preferably, the method accommodates how a sensor is attached to a participant. Adapting orientation converts sensor data so that acceleration and other kinematic properties are aligned to a coordinate system of the participant. The orientation of the activity monitoring device can be described in terms of yaw, pitch, and roll wherein a yaw axis is aligned with a defined up-down vertical axis (e.g., aligned with gravity), the pitch axis is aligned with an axis orthogonal to the left or right side-view of a participant, and the roll axis is generally aligned with the direction of motion (e.g., the forward/backward direction). Adapting orientation of kinematic data sensing to participant orientation preferably calibrates the pitch and roll of how the activity monitoring device is affixed to a participant as shown in FIG. 6. Pitch is characterized as the tilt or more specifically the rotation in the sagittal plane. Roll is characterized as the drop or more specifically the rotation in the coronal plane. Depending on the design of the activity monitoring device, the pitch and roll can vary between uses. Adapting orientation can additionally calibrate yaw. Yaw is characterized as the rotation of the activity device and more specifically the rotation in the transverse plane. Yaw is more preferably classified in one of two orientations with an activity monitoring device facing forward or backwards when the activity monitoring device is structurally designed to orient in one of two directions. Other variations, may promote activity monitoring device oriented in only one standard direction wherein that yaw orientation can be assumed.

Adapting orientation preferably includes taking sensor readings at different positions and defining a data transformation. The data transformation is preferably a rotation, implemented via rotation matrices, quaternions, or other suitable transformations. Adapting of orientation can be performed during an initial calibration stage, but may additionally or alternatively be performed periodically or continuously during an activity. When multiple inertial measurement systems are used, each is preferably calibrated so that orientation is adapted to a substantially consistent or shared participant orientation. Additionally, adapting the orientation of kinematic data in a multiple inertial measurement system variation can include calibrating the kinematic sensor data of one sensor device to a calibrated sensor device. A shared coordinate system can enable more direct comparison of kinematic properties detected by the set of inertial measurement systems. For example, a pelvic sensor device may be calibrated and then used to adapt the orientation of a foot-mounted sensor device.

In a similar manner, Block S124, which includes determining a rotational reference of a body part, functions to determine a default body position for a body part. Determining a rotational reference preferably determines a base pelvic tilt reference. By determining a base pelvic tilt reference, pelvic rotations and angles during other activities such as running can be reported based on offset from the base pelvic angles. For example, the running pelvic tilt can be calculated as an offset from the base pelvic tilt. The method may additionally or alternatively determine base positions for the foot, leg shank, thigh, or any suitable body part such as the upper- or mid-back region, and the neck. The base pelvic tilt position is preferably based on the orientation during some particular type of activity or portion of an activity. For example, the rotational position of the pelvis is preferably zeroed at a base angle during walking. The base pelvic tilt position may alternatively be based on a standing position, a sitting position, or any suitable position or activity. The base position can be an average, a median, a mid-range value, or any suitable point. In one implementation, the base pelvic angle is the average of the pelvis angle when walking. An initial rotational reference of a body part is preferably established before an activity or during the beginning portion. A rotational reference may additionally or alternatively be established at any suitable point. Additionally, a rotational reference can use historical data of a participant or multiple participants. Rotational references can additionally be established for different types of actions. For example, standing, walking, running, biking, and other actions may have different rotational references. The rotational reference is preferably based on the orientation of Block S122. In one variation, the rotational reference may be assigned based on the orientation metrics during a particular stage of an action, which may utilize the segmentation of Block S130. For example, the rotational reference of a runner may be based on the midstride orientation or alternatively at the full stride stage orientation of the inertial measuring system.

Figure 17:
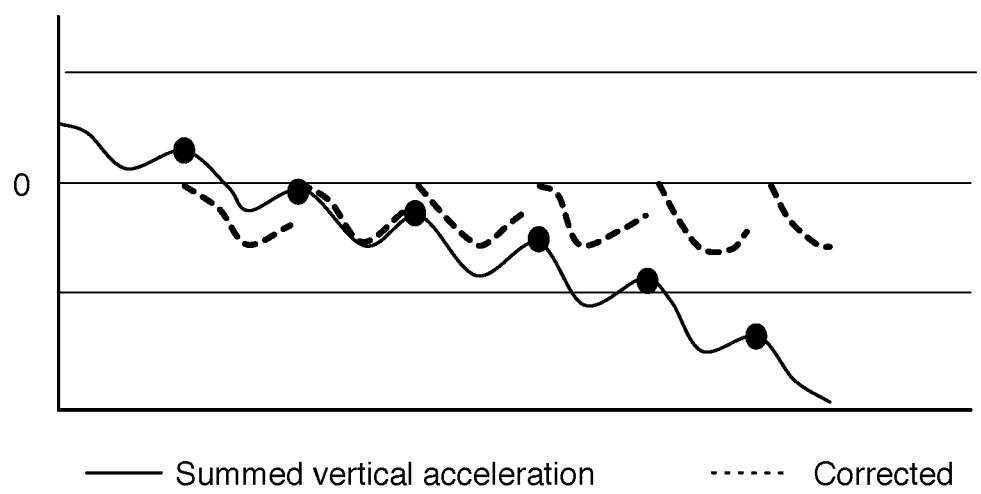
FIG. 17 is a graph representation of segmenting accelerometer data.

Block S130, which includes segmenting at least a subset of the kinematic data streams, functions to determine or identify the timing for each portion of interest of an activity. Segmenting the biomechanical data preferably classifies time windows of the data streams into consistently detected segments based on a repeated motion or predetermined motion. In the case of walking or running, steps can be identified and used to define the segments. Herein, step segments are used as the exemplary form of a segment, but a segment could alternatively be any portion of an action such as an arm stroke, a swing, a rowing motion, a pedal, or any suitable action of interest during an activity. Determining step timing preferably achieves substantially consistent windowing within a step. Segmenting is preferably based on the kinematic data stream for vertical velocity, which can be derived from the vertical acceleration kinematic data stream. Preferably, segmenting identifies a segmentation point by identifying a local maximum in the sum of vertical accelerations. Integration error may result in drift and a baseline reset correction can be used as shown in FIG. 17. A filtered accelerometer vector length that uses all three axis components of acceleration may alternatively be used to segment the steps. Segmenting may additionally be based on lateral or forward-backwards accelerations, velocities, displacements, or rotational quantities independently of, or in addition to, segmenting based on vertical velocities or accelerations.

The step segmenting process can provide a consistent reference frame for analyzing and generating multiple biomechanical signals. Step segmenting preferably generates a sequence of timestamps that are used as a marker for a new step cycle. Step segmenting preferably has a consistent segmenting phase (i.e., the start of a new step segment corresponds to a substantially similar motion in the step motion). Once step timing is determined, data can be segmented according to the steps. Segmentation could alternatively be generated for a stride where a stride is two consecutive steps, and a step is taken by the right or left leg. Accordingly, step segmentation could include stride segmentation. Since strides are substantially consistent between two strides (unless a change in motion such as going from a walk to a run occurs), step timing can additionally provide a predictive window for transforming kinematic data into biomechanical signals. Step segmenting can additionally be used in producing a step count in transforming the kinematic data into a set of biomechanical signals. In one variation, the step segmenting and/or step counting can additionally be used as a biomechanical signal.

Figure 8:
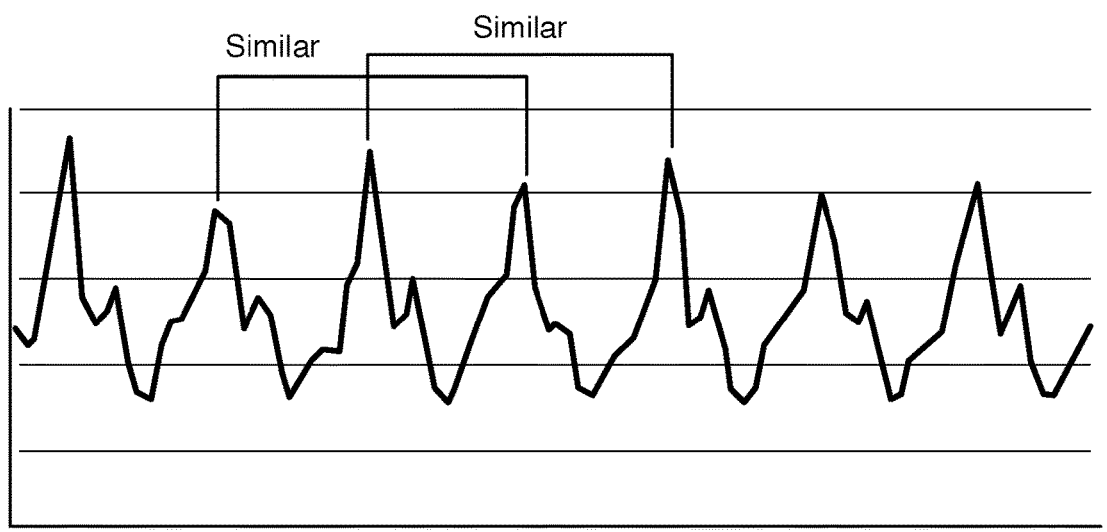
FIG. 8 is a graphic representing the kinematic similarities between offset steps.

Segmenting can use various techniques for step detection. In one variation steps can be segmented and counted according to threshold or zero crossings of vertical velocity. A preferred approach, however, includes counting vertical velocity extrema. Identifying extrema in the vertical velocity signal can provide reliable timing information and can be used in finding rhythm constraints without having to apply a Fourier transform. Running and other activities may be quasi-periodic patterns with no guarantee of periodicity. For example, a user jumping over a puddle will not yield a specific rhythm. Approaches to segmenting described herein may address such quasi periodic tendencies of the data. Identifying extrema in vertical velocity preferably accounts for quasi-periodic step patterns. Periodic step patterns can include the pattern in timing, amplitude, and direction of vertical velocity for alternating steps. An increased similarity in kinematic properties of two steps may be observed with steps displaced by an odd number of steps—steps with the right leg will have more in common with other right leg steps, and a step with the left leg will have more in common with other left leg steps as shown in FIG. 8. Identifying extrema for left steps and right steps may use different thresholds and conditions to account for such a differences.

Identifying extrema preferably includes summing vertical acceleration values or otherwise approximating vertical velocity. A local extrema is preferably selected within some windowing constraints. The selected step maximum can be used as a step segment divider indicating the beginning/end of a step. Offsetting the vertical acceleration and/or smoothing the data may be used as preprocessing operations but could similarly be applied afterwards as a resetting operation. The detected vertical velocity may oscillate with an acceleration offset caused by gravity. In one implementation, the method comprises removing an offset bias of gravity, which functions to offset the vertical velocity to oscillate about zero. High frequency oscillations or jitter in the vertical velocity are preferably filtered. For example, a lowpass filter can be applied to the vertical velocity.

Identifying segmentation points through local extrema preferably includes identifying maximum and minimum extremas. Local extrema may be identified in a variety of ways. Preferably, the previous and subsequent vertical velocity data points are compared to a currently inspected vertical velocity data point. If the selected data point is greater than the previous and subsequent data points, then that data point is a local maximum. If the selected data point is less than a previous and subsequent data point, then that data point is a local minimum.

$$\tilde{a}_{t-1} < \tilde{a}_t > \tilde{a}_{t+1} \Rightarrow t_{max} = t$$

$$\tilde{a}_{t-1} > \tilde{a}_t < \tilde{a}_{t+1} \Rightarrow t_{min} = t$$

More specifically, a set of previous values are inspected. The number of values to inspect to identify local extrema may depend on the sampling frequency. Alternative approaches may include inspecting additional neighboring sample points (e.g., sample points two or three removed). Considering a larger window of data points can function to reduce jitter without filtering. A magnitude threshold may additionally be used to conditionally select a maximum based on its magnitude. The magnitude of a maximum is the difference between the maximum and the previous minimum.

$$h(t_{max}) = \tilde{a}t_{max} - \tilde{a}t_{min}$$

$$h(t_{max}) > \varepsilon t_{max}$$

The magnitude threshold can be recalculated periodically. When sampled at a frequency of 25 Hz an exemplary magnitude threshold may be:

$$\epsilon = \frac{1}{40} \max_{t > t-50} \tilde{a}_t$$

Additionally, step segmenting and corresponding step counting may include a set of detection conditions. A step sequence threshold can be a condition on the number of identified step segments within a defined time window. For example, two to five steps may be counted in one second when running. In one variation, there can be a timeout condition, wobble condition, range condition, shake condition, and/or an area condition. The various conditions can be used in validating the detection of step segments or setting a confidence level in step segmentation. If particular conditions are not met, the method may assert that a user is not performing the activity (e.g., running) and discard erroneous step data.

Timeout condition specifies a number of maxima that can be detected within a time window. The timeout condition functions to not count activity that is not related to walking, running, or otherwise taking repeated steps. For example, a maximum may be rejected if a second one is detected in less than a fifth of a second.

A wobble condition functions to verify that the time duration of each step is sufficiently consistent. The time between maxima is measured and then used to create an average wobble time. If the average wobble time falls below some threshold, the condition is not satisfied. In one implementation, 0.15 seconds can serve as a good wobble threshold.

The range condition can be another condition based on step duration. The range condition preferably uses a comparison of step duration of steps of the same foot (i.e., alternating step segments). The range condition is preferably satisfied if the difference between the maximum step duration and the minimum step duration over a set of consecutive steps of the same foot is less than a set threshold. For example, if the difference in step duration of consecutive right steps or left steps is less than 0.24 seconds, the step segmenting and step counting can continue.

A shake condition functions to consider an assumption that the direction of acceleration should be similar for steps with the same foot and dissimilar between left and right steps. A person will have some amount of swing back and forth for each step, which the shake condition may characterize and use as a condition in step segmenting and detection. According to a shake heuristic, the angle between right and left step accelerometer vectors is preferably a positive angle, and the angle between two right or left step accelerometer vectors is a substantially small angle and zero in the ideal case. In one implementation, shake can be parameterized as the difference between a different-leg angle and a same-leg angle. The shake condition can accept step segmentation when the shake for a sequence of steps is above a set value as shown below. Defining $\sin(\vec{v}_1, \vec{v}_2)$ to be the sine of the angle between two vectors $v_1$ and $v_2$, shake at the $n^{th}$ maxima is given by:

$$S_n = \sin(\vec{a}_n, \vec{a}_{n-1}) - \sin(\vec{a}_n, \vec{a}_{n-2})$$

The shake criterion is satisfied when:

$$S_4 + S_5 + S_6 + S_7 > 0$$

The area condition enforces that quicker steps have higher maxima. An area value for a step segment can be defined as an extrema height times the duration of the step. The extrema height is the difference between the maximum value and the previous minimum. In one variation, the area condition can be set such that the combined area of four previous steps is greater than a threshold. In one implementation, the area threshold was 0.7.

Another variation of segmenting steps can include using a leg based inertial measurement system. Preferably, a lower leg inertial measurement system is used, but a thigh or alternative leg position can be used. Preferably, an inertial measurement system is used for each leg, but a single leg may alternatively be monitored. The kinematic data relating to the forces, acceleration changes, and additionally the rotational change that occurs during foot contact with the ground may be more pronounced through a leg-based inertial measurement system. Accordingly, the segmentation of a step may be more reliably detected. The foot is limited in its movement by the ground, which provides a hard stop to any downward displacement when the foot makes contact. One heuristic could analyze the vertical velocity of a foot for a zero velocity as an identifier for step segmentation. Step segmentation provided by a leg inertial measurement system is preferably synchronized with a pelvis inertial measurement system so that step segmentation can be applied to other biomechanical signals such as pelvic centric biomechanical signals. In one variation, the step segmentation can be cooperative where the kinematic data streams from multiple inertial measurement systems are used in combination. In another variation, a first stage of step segmentation can be performed using different inertial measurement systems and then a composite step segmentation is generated by using multiple step segmentation approximations. For example, the step segmentation may be a weighted average of a pelvic step segmentation and a foot step segmentation.

Block S140, which includes generating a set of biomechanical signals from the kinematic data streams, functions to parameterize a set of primitives from which the motion properties of an activity can be monitored and acted on. During generation of the biomechanical signals, the kinematic data is transformed and processed into a set of biomechanical signals preferably transforming the normalized kinematic data into biomechanical signals of segmented activity. The biomechanical signals are preferably based on step-wise windows of the kinematic data streams—looking at single steps, consecutive steps, or a sequence of steps. A biomechanical signal is preferably a time series signal with values that characterize a biomechanical property during a segment. For example, ground contact time signal is a sequence of values reflecting the ground contact time during discrete steps (or a window of steps). Discrete action specific metrics can be utilized in generating coaching, targeted performance feedback, equipment recommendations, health checks, and/or other applications of the biomechanical signals in block S140 that go beyond general performance metrics. In another variation, the step-wise windows may be based on left or right step segments.

Figure 9:
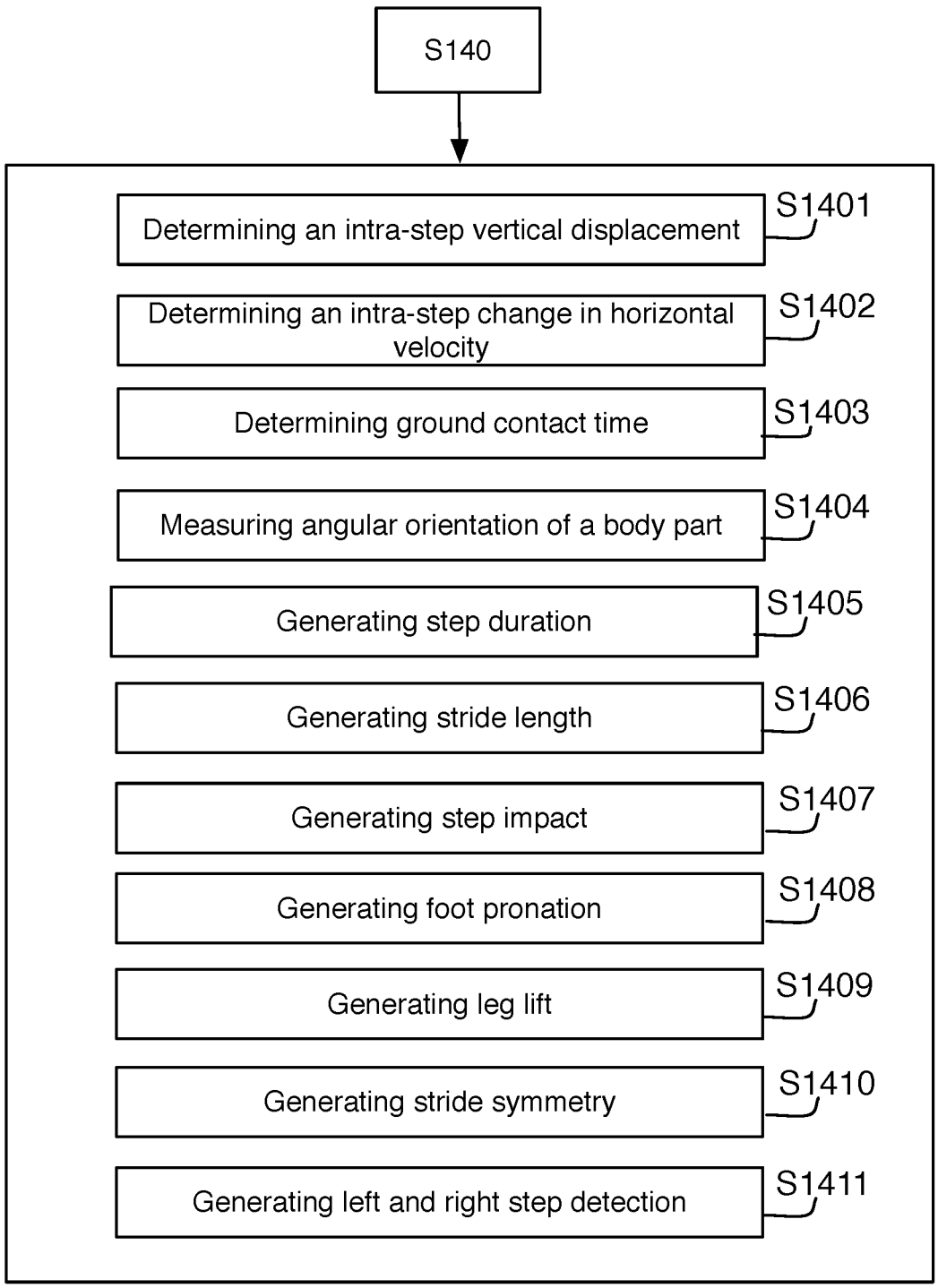
FIG. 9 is a flowchart representation of a variation for transforming the kinematic data into a set of biomechanical signals.

The set of biomechanical primitives can include ground contact time, braking, pelvic rotation, pelvic tilt, pelvic drop, forward velocity properties of the pelvis, and/or vertical oscillation of the pelvis. Accordingly, transforming the kinematic data into a set of biomechanical signals can include determining an intra-step vertical displacement S1401, determining an intra-step change in horizontal velocity S1402, determining ground contact time S1403, and measuring angular orientation of a body part S1404 as shown in FIG. 9. Additional or alternative biomechanical primitives may alternatively be used. For example, transforming the kinematic data into a set of biomechanical signals can include generating step duration S1405, stride length S1406, step impact S1407, foot pronation S1408, leg lift S1409, stride symmetry S1410, left and right step detection S1411, or other stride-based biomechanical signals as shown in FIG. 9. The above biomechanical primitives can have particular applicability to walking, running, and standing usecases. Alternatively, use cases may use alternative biomechanical primitives relating to acceleration, deceleration, change of lateral direction, jump duration, and other suitable properties of performing some activity.

As shown in FIG. 6, a set of biomechanical signal primitives can be generated from a processing framework utilizing one or two stages of data stream integration and error correction. The data stream source can be accelerometer data and/or gyroscopic data. In some variations, metrics from multiple processes are used in combination in determining a biomechanical signal.

More specifically, a variation of the method utilizing the processing framework can include generating a first integration data set through data integration and baseline error correction across the set of segments of the normalized kinematic data stream S141, determining a first biomechanical signal that is partially based on the first integration data set, S142, generating a second integration data set through data integration and baseline error correction across the set of segments of the first integration data set S143; determining at least a second biomechanical signal that is at least partially based on the second integration data set S144; generating a gyroscopic integration data set through data integration of gyroscopic kinematic data and baseline error correction S145; and determining pelvic rotation and pelvic drop signals at least partially based on the gyroscopic integration layer and the rotational reference of the pelvic region S146. As shown in FIG. 6 ground contact time may be based on the first integration data set and step segmentation; braking may be based on the first accelerometer integration data set; vertical oscillation and forward oscillation may be based on the second accelerometer integration data set; and pelvic rotation, pelvic drop, and pelvic tilt can be based on the first gyroscopic integration data set; and biomechanical signals such as cadence may be based on step segmentation or any suitable set of data sets.

Figure 10:
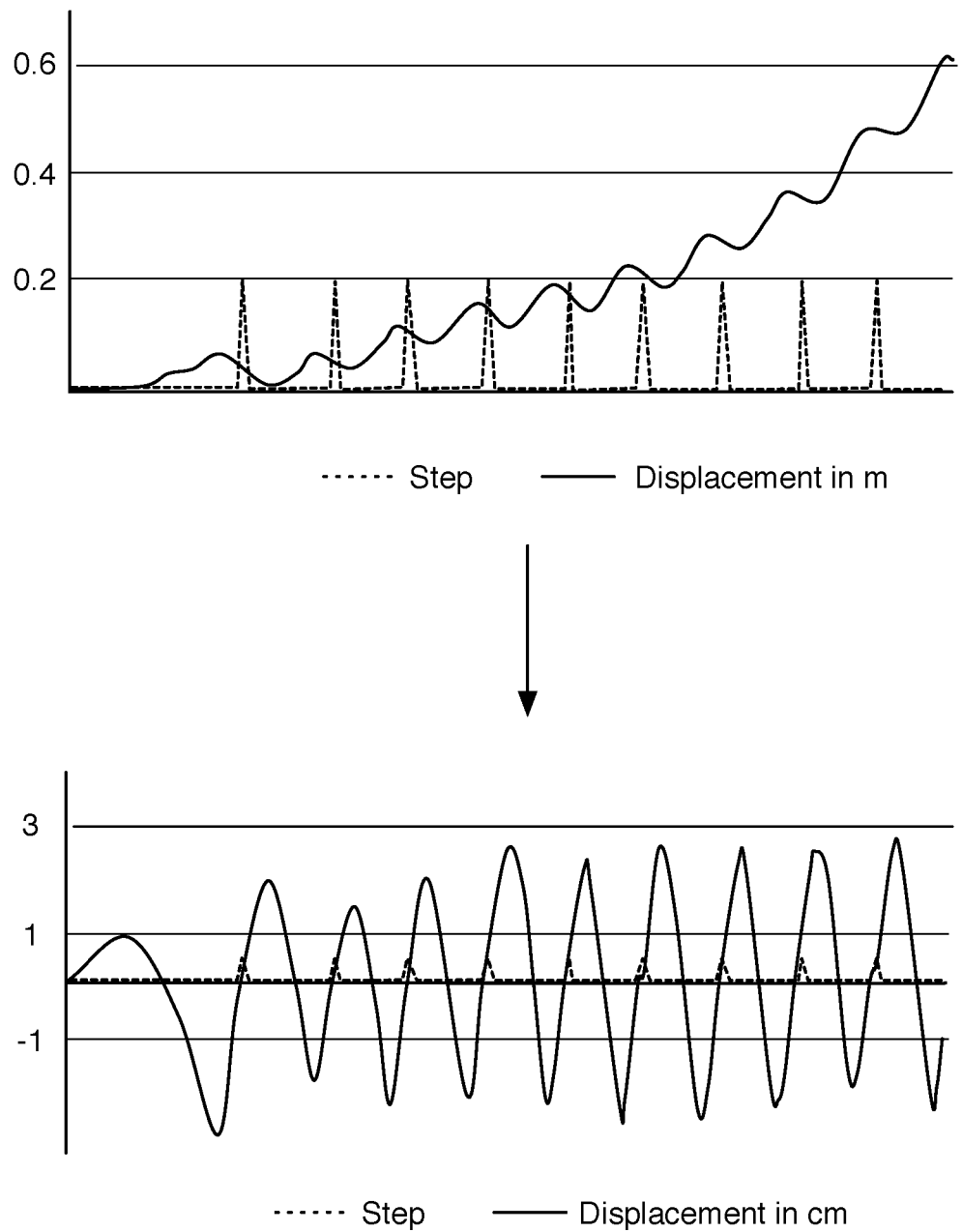
FIG. 10 is a schematic representation of localizing to a fixed displacement.

Block S1401, which includes determining an intra-step vertical displacement, functions to characterize the up and down bounce when moving. Intra-step vertical displacement provides a measurement for the difference between a sensor's largest and smallest distance from the ground during a step. Determining an intra-step vertical displacement can include using a kinematic data stream segmented by steps and integrating vertical acceleration twice to compute the vertical displacement. Integrating vertical acceleration twice preferably includes correcting for integration error. One error correction approach can employ the error correcting heuristic based on the observation that a sensor's velocity and displacement from the ground should be substantially consistent at consistent points in a gait cycle. Preferably determining an intra-step vertical displacement can include integrating a normalized accelerometer data stream, performing zero baseline error correction on the integrated accelerometer data (resulting in corrected velocity data), integrating the corrected velocity data, and performing zero baseline error correction on the integrated velocity data. In correcting vertical velocity with zero baseline error correction, the error correction can utilize the top of the bounce or bottom of the bounce as the zero velocity point. Correcting integration error for displacement can use a localizing displacement approximation based on this consistent displacement of the lowest point. At least one point of a vertical displacement calculation within a step segment is localized to a fixed displacement. The baseline error correction utilizes the step segmentation to account for signal drift during integration of the kinematic data streams. Vertical displacement is then based on the difference between the maximum and minimum vertical displacements between two localized points as shown in FIG. 10. Linear error correction, quadratic error correction, or any suitable error model can additionally or alternatively be used in correcting for error. Intra-step horizontal displacement can similarly be calculated.

Block S1402, which includes determining an intra-step change in horizontal velocity, functions to characterize the forward-backward fluctuations when walking or running. The intra-step change can be based on velocity and/or displacement. A runner will move forward with a fluctuating forward velocity that generally can vary based on the point in a step. The intra-step change in horizontal velocity can be calculated in a similar manner to the intra-step vertical fluctuations of S1401. The intra-step change in horizontal velocity may be used as a characterization of the varying forward propulsion during a step. A participant will typically not move with an absolute constant speed. An activity such as running will frequently have small forward speed changes with each step or stride. For example, a slight speed increase may occur when a participant pushes off with each leg. Whether a step is left or right can additionally change the fluctuation of the forward velocity. There can be various ways of characterizing the intra-step change. In a first variation, the measurement can be the difference between the maximum and minimum forward speeds during a step. In another variation, the measurement can be the difference between the average forward speed during a step and the minimum speed during a step. The horizontal velocity of block S1402 preferably refers to the forward velocity of the pelvis during the activity. Determining an intra-step change in horizontal velocity can use a sampling frequency of 50 Hz or greater at a +/−4 g sensitivity or greater when sensing kinematic properties in the waist region. Alternative sampling frequencies or sensitivities may alternatively be used. Intra-step change in vertical velocity may similarly be calculated.

Figure 11:
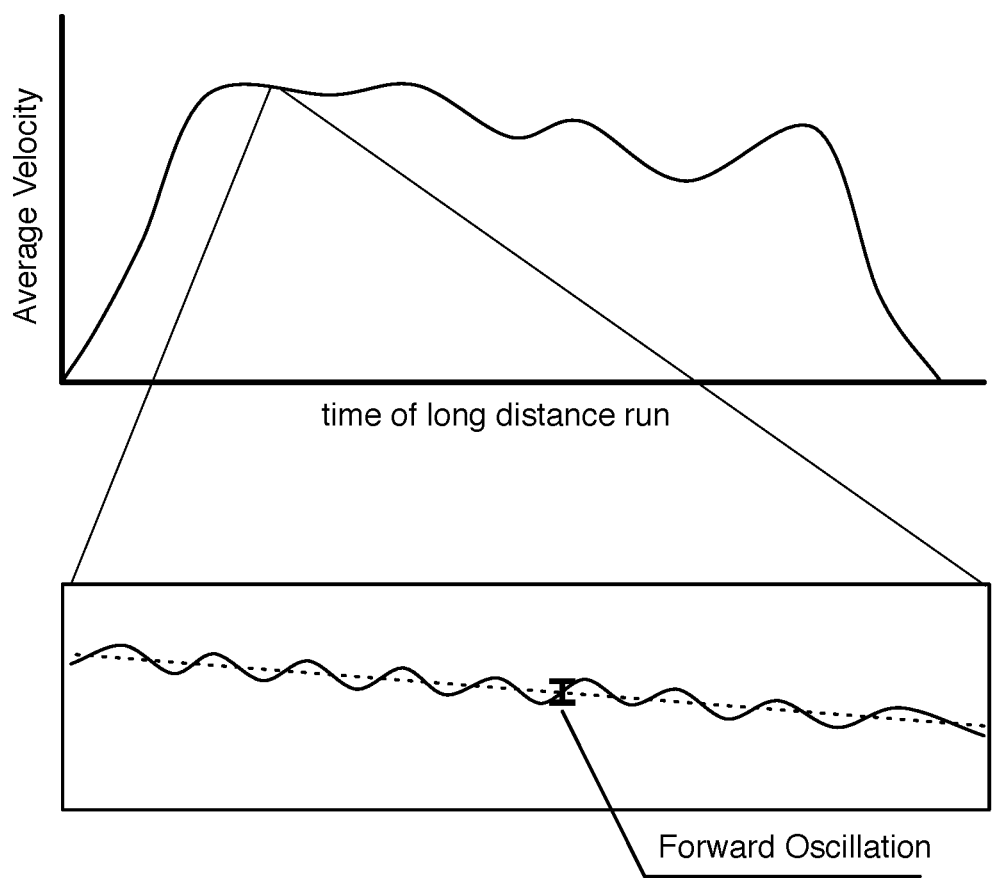
FIG. 11 is a schematic representation of a process for intra-step horizontal velocity change.

Determining the intra-step change value preferably uses the adapted orientation of the sensor to indicate forward (or backwards) motion along the roll axis. Alternatively, multiple acceleration axes can be combined to provide acceleration in the forward motion. The generation of the horizontal intra-step changes can include integrating a normalized accelerometer data stream and performing baseline error correction on the integrated accelerometer data. The roll-axis acceleration is then integrated for each step segment to provide a velocity calculation as shown in FIG. 11. The difference between the highest and lowest velocity value within a step can be set as the measurement for intra-step change (i.e., a braking signal). The difference between the minimal velocity point and the average difference between the maximum and minimum velocity may alternatively be used as the measurement for the intra-step change, which may be referred to as a braking biomechanical signal. Measurements can be averaged over previous steps to provide an averaged measurement value. A biomechanical signal for intra-step change in horizontal velocity can additionally be generated for each leg. Linear error correction can be used. Similarly, localizing velocity to a baseline velocity can account for data integration error. A base velocity can use a moving average velocity approximation. For example, a reference speed may be determined using GPS or other techniques for tracking high-level velocity measurements. Each step preferably oscillates around the base velocity. The step segmentation can be used to account for integration drift away from a baseline velocity. The baseline velocity is preferably dynamically updated to correspond to the overall velocity of the participant.

In an alternative approach, determining intra-step change in horizontal velocity can utilize kinematic data from leg-based inertial measurement systems. The initial contact of a foot with the ground contributes a large part of the braking force during a step. Analyzing the acceleration data from a sensing point on the foot can provide high resolution. Additionally, the braking biomechanical signal can be specified for the right and left leg.

Block S1403, which includes determining ground contact time, functions to characterize how long a foot is in contact with the ground when walking or running. The ground contact time preferably provides a time-based measurement of how long a foot is in contact with the ground during a step. In one variation, the ground contact time can be estimated as a running average for both feet. For example, the average time duration a foot is in contact with the ground can be reported as a running average of the amount of time a foot is in contact with the ground for each step or stride. In another variation, the ground contact time may be reported for a first and second foot. The method may additionally identify the first and second foot as a right and left foot. In one variation, right and left differentiation can be accomplished through single-point activity sensing. Multi-point sensing could additionally be used in differentiating right and left biomechanical signals. A ground contact time can be reported for the right foot, and a ground contact time can be reported for the left foot. Additionally, a ratio of foot contact can be generated based on the comparison of the right and left foot ground contact times, which may function to indicate any favoring of one leg over another. The ground contact time can be reported as a time, but may alternatively be reported as a percentage of step duration.

Determining ground contact time in a first variation includes segmenting the vertical velocity data by steps and taking the difference between the time of the maximum vertical velocity and the time of the minimum vertical velocity within each step cycle. In this variation, the maximum vertical velocity is selected as an event corresponding to the time of when the foot leaves the ground (i.e., "toe-off"), and the minimum vertical velocity is selected as an event corresponding to when the foot makes initial contact with the ground.

Determining ground contact time in a second preferred variation can include measuring the time difference between the minimum vertical acceleration and the time of the minimum vertical velocity, adjusted by a linear transformation or other transformation. The minimum vertical velocity will correspond to when an increasing vertical acceleration crosses zero. At lower sampling rates, the time when vertical acceleration crosses zero can be in between sample points. A linear interpolation between negative and positive values of vertical acceleration and identification of a zero point can be used to refine the minimum vertical velocity time. Similar interpolation may be applied to identifying a minimum vertical acceleration. In one variation, a three-point interpolation for a parabola or other quadratic may be used. In another variation, determining ground contact time can include measuring the time difference between the time of the minimum forward velocity and the time of the maximum forward velocity and applying a linear transformation.

In another variation, an additional sensor or sensors may provide kinematic data sensed at or near the foot. For example, a sensor may be worn on each shoe. Foot sensor data can be used to provide higher resolution or refinements to the above methods or provide additional kinematic events acting to identify the beginning or end of foot contact. The ground contact time may be determined using other suitable techniques.

Block S1404, which includes measuring angular orientation of a body part, functions to quantify the kinematic motion properties of at least one body part. In the preferred implementation with a sensing device positioned in the waist region, measuring angular orientation of a body part includes measuring pelvic tilt and/or range of rotation during an activity. The angular tilt during an activity is preferably compared to the calibrated reference angular position of the pelvic region. The angle can be reported for a single axis of rotation but can additionally account for three-dimensional rotation in multiple axes. Measuring pelvic tilt can address questions such as whether a participant leans to the right or left or whether the participant has a forward or backwards tilt when running. The pelvic angular orientation range is preferably based on the range of pelvic rotation during a step and/or stride. The individual step or stride rotational range is preferably tracked. A running average of rotational range across some set number of previous steps can be used in producing a pelvic rotation range for a particular time instance. The angular orientation of other body parts may alternatively or additionally be monitored depending on the positioning of a sensing device.

In block S1406 step length measures the distance covered during a step. Step length can be an average of right and left steps, but step length may additionally be determined for each leg. Step length can be reported for each step but may alternatively be a running average of steps within a particular window. A forward acceleration data stream for a foot is preferably segmented by steps and integrated twice to compute the forward displacement. Integration error can preferably be corrected. Baseline error correction may be used as described above to correct for integration error and drift. In this single or multi-point variation a sensor device is positioned on at least one leg and more preferably a foot or lower leg region. Calculation heuristics can be included that take into account the distance traveled by each foot and a reference displacement determined by GPS measurements. Additionally or alternatively stride length may be measured as the distance covered by two consecutive steps.

In another variation, stride length signal may be generated from a pelvic-positioned sensor device. The pelvic region of the body is isolated from stride-based displacements, but the determination of a stride length can include training a stride length estimation model that utilizes detectable biomechanical patterns. A stride length estimation model can be dependent on braking, cadence, vertical oscillation (i.e., bounce), and/or other biomechanical signals or factors. Estimating a stride length from a pelvic sensor preferably includes training the model during a position-tracked session. The GPS of a sensor device, a smart phone, or some other computing device preferably collects gross displacement data of a participant while biomechanical signals are also collected. Stride length estimations may be generated using the step segmentation. Additionally, a set of biomechanical signal factors are generated that set the correlation between biomechanical signal factors and stride length. Such training may be performed for each participant. The training could additionally be updated periodically, which may function to account for changes in stride length patterns with changing fitness and health of a participant. In another variation, a pre-generated stride length estimation mode can be assigned to a participant based on demographics (e.g., age, sex, height, weight, etc.), fitness level (e.g., amount of activity, activity performance level, etc.), or other factors. The pre-generated stride length estimations may be generated from multiple other participants or collecting data from prototypical test subjects.

A stride length estimation model can then be applied to estimating stride length absent gross displacement input. For example, a stand-alone sensor could generate stride length and even running distance without use of a GPS. Stride length is correlated to pace and the above approaches could similarly be applied to a pace metric.

Determining foot pronation functions to characterize the rotation of a foot during a step. Foot pronation can characterize the rotational angle of a foot during ground contact. Foot pronation can alternatively characterize the path of a foot during a step. The contact angle and the foot path variations may both be used as biomechanical signals. Determining the contact variation uses the step segmentation to select at what point to analyze the foot angular orientation. Determining the foot path pronation includes tracking the relative displacement of a foot during each step. The foot will generally go through a repeated path during a step. Some people have very linear foot paths when they run. Others swing their foot in (underpronation) or out (overpronation) while they run. The foot path pronation biomechanical signal can characterize the deviations form a normal path.

Figure 12:
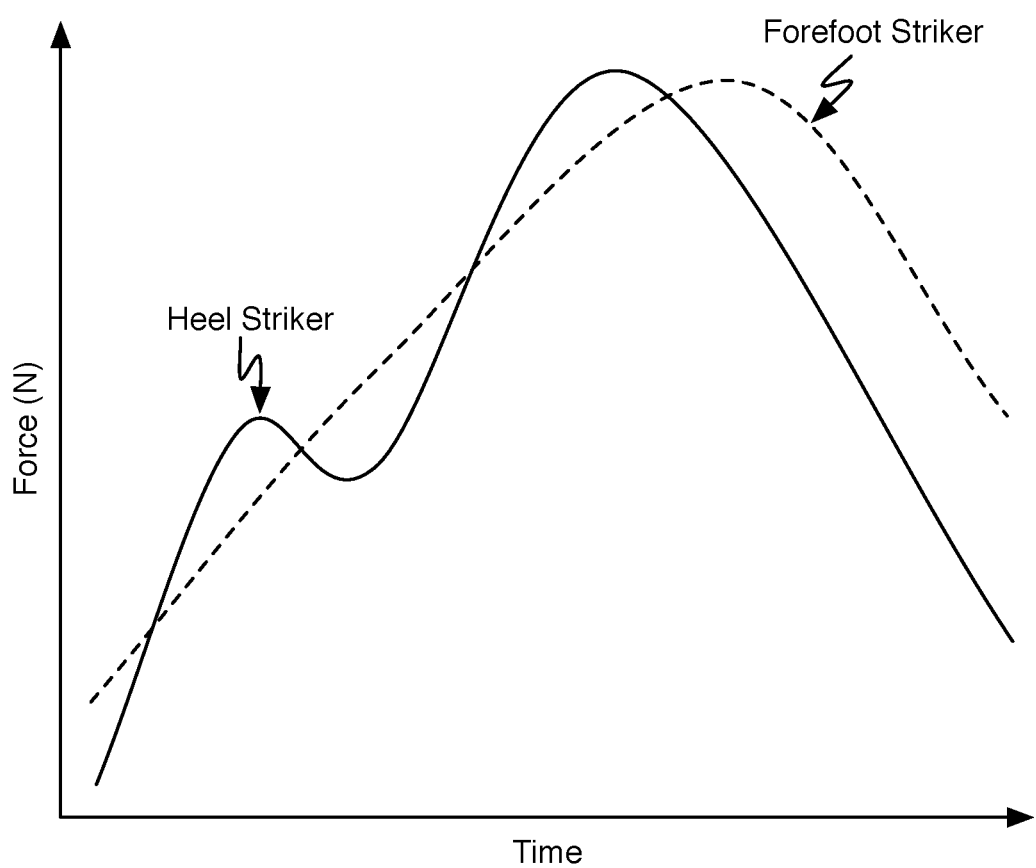
FIG. 12 is a graph representation of a body loading signal.

In another variation, a ground reaction force impact signal can be determined. A force impact signal is experienced during footstrike force over time during ground contact. The body loading signal is preferably a set of data points but may alternatively be converted into a value metric or a classification. The body loading signal may indicate if a runner is a heel striker or a forefoot striker as shown in FIG. 12. Runners who strike with their heel may have a higher risk to injury. The force is preferably determined from the vertical acceleration forces of the foot. More simply a step impact signal (e.g., a shock signal) in block S1407 can be generated from the local maximum of vertical acceleration during a step.

In another variation, a knee related biomechanical signal can be generated based on a thigh positioned inertial measurement system. Knee related biomechanical signals could include the upper leg rotational range, the knee-bending angle, and/or the knee lifting distance. The upper leg rotational range characterizes the angular range of the thigh during a step. The knee-bending angle characterizes the minimum angle between the thigh and the shank (e.g., when the leg is lifted). The knee-bending angle can involve processing kinematic data of a thigh inertial measurement system and a lower leg inertial measurement system on the same leg. A knee lifting distance measures the vertical displacement of the knee, which may utilize kinematic data from the upper and lower leg. In another variation, a pelvis and shank sensor system can estimate knee angle by calculating the individual vertical displacement of the pelvis and shank sensors.

Figure 13:
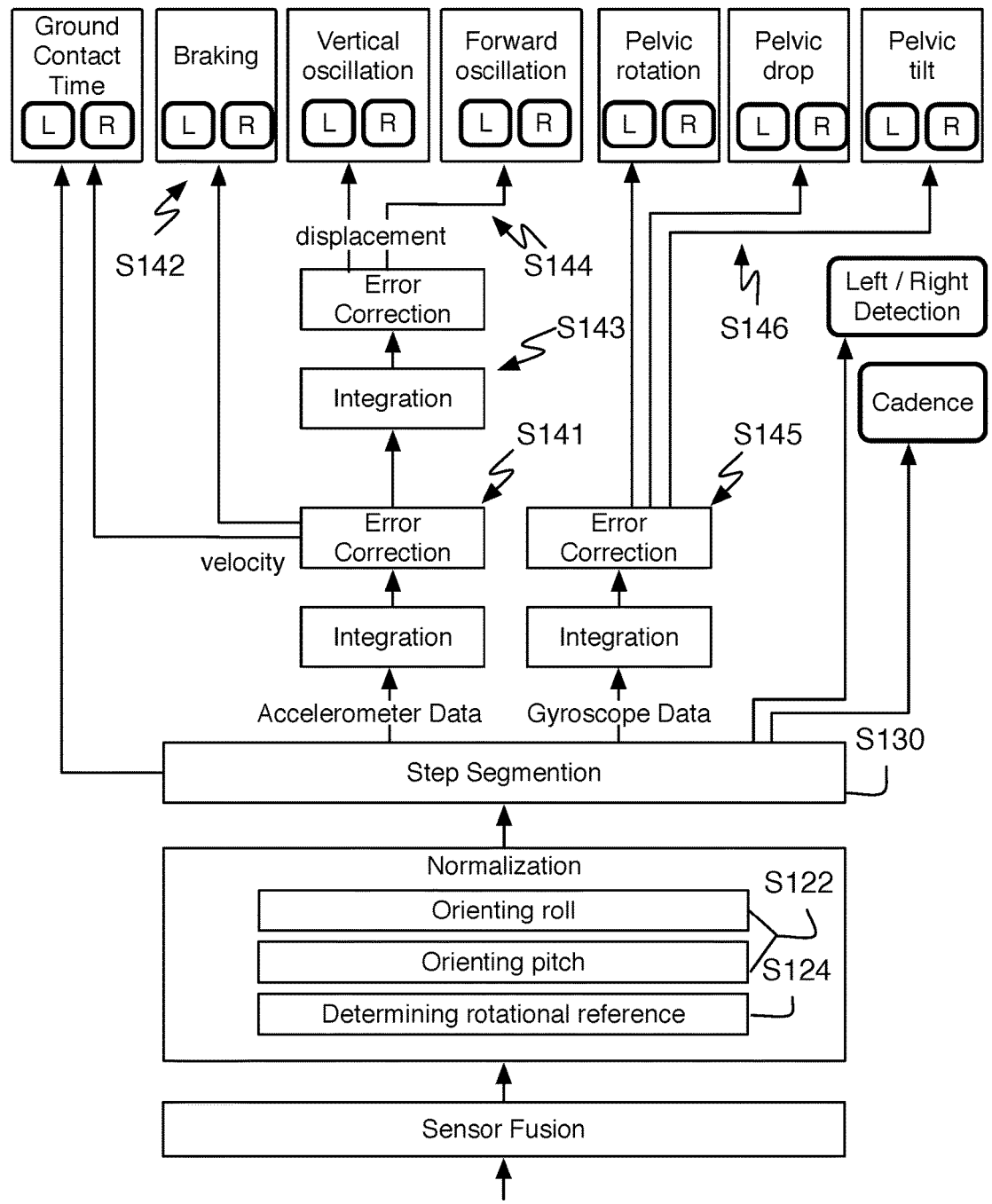
FIG. 13 is a detailed flowchart representation of a processing framework with left-right classification.
Figure 14:
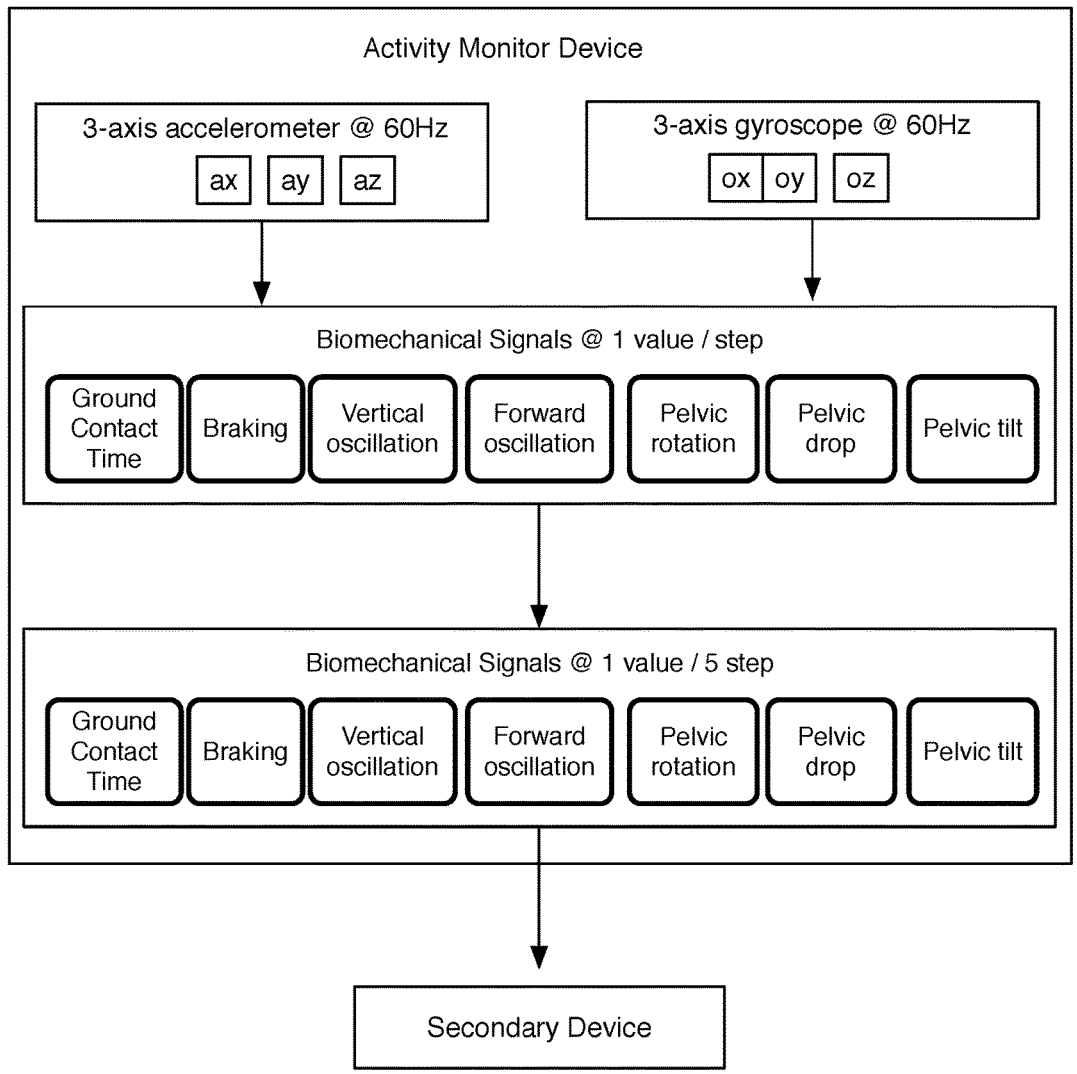
FIGS. 14 and 15 are schematic representations of data compression through biomechanical signal processing.

In another variation, generating a biomechanical signal can determine a left-right biomechanical signal, which functions to differentiate between actions alternating between right and left sides. More preferably, this includes classifying segments as left- or right-sided actions. Variations of an action such as stepping with different legs can be classified as distinct biomechanical signals (or a sub-category of biomechanical signals) as shown in FIG. 13. Left-right signals preferably refers to actions that alternate between a participant's left side and right side, but can similarly apply to any multi-sided action. The left-right signals can be applied to distinguishing between a step with a right leg and a step with a left leg for a walking or running activity. Left-right leg signals could also be used to distinguish between left and right swim kicks, left and right bike pedal pumps, or other leg actions. The left-right signals may additionally or alternatively be applied to actions performed by the right arm or left arm such as a swim stroke, a rowing stroke, or any suitable action. Herein, the left-right signals are described primarily from the running use-case perspective, but can be similarly applied to other use cases.

Detecting a left-right biomechanical signal preferably includes identifying side bias in the kinematic data and/or other biomechanical signals.

In one variation, the normalized kinematic data streams determine a vertical axis and a forward-backward axis. A left-right axis can be determined from these two perpendicular axes. Left and right strides can be determined by monitoring the angular oscillation at a pelvic sensing device during a step segment. Gyroscopic data providing angular velocity around a vertical axis through the sensor towards earth can be used. In one variation, the left foot is determined if the angular velocity at the beginning of the step segment around the vertical direction measured by the gyroscope is less than zero, otherwise the right foot is determined. The angular velocity can be inspected at the beginning of a step segment. The sum of angular velocities over a whole step could alternatively be used for detecting a bias. Once left and right steps are identified the alternating pattern can be assumed to continue during subsequent step segments. However, continuous or periodic left-right detection can be performed to correct or verify accurate classification of steps. Additionally, anomalies in kinematic data or biomechanical signals can trigger an event to perform left-right detection. For example, after a participant stops or trips, the biomechanical signals may satisfy a condition that restarts the left-right detection.

In one variation, left-right classification can be determined through a sensor device positioned on one leg of a participant. The kinematic forces may be felt more strongly in a side-biased sensor device. Stronger forces evident in the kinematic data during a foot contact point of a step segment can indicate that the monitored side is currently making a step. Two side-biased sensor devices with one on each side can further address the challenge of detecting the current side.

A left-right detection in one variation may be used in a variety of ways. Preferably, the left-right detection is used to classify the biomechanical signals of the step segments such that at least a subset of biomechanical signals are classified into left and right biomechanical signals. For example, there could be a left and right braking biomechanical signal, a left and right ground contact time, a left and right vertical oscillation, and a left and right forward oscillation. Health issues, form issues, strength issues, and other insights may be acted upon in performing left-right detection. The left-right detection may additionally be used in calculating other biomechanical signals. For example, the left-right oscillations may be corrected when calculating particular biomechanical signals such as pelvic rotations.

Block S140, which includes applying the set of biomechanical signals, functions to use the biomechanical signals for altering a user feedback device, directing the operations of the activity monitoring device, and/or causing any suitable change.

In a first variation, applying the set of biomechanical signals can include communicating the biomechanical signals. The biomechanical signals can be communicated to a system or service. The biomechanical signals can be provided in a data format, wherein further analysis of the biomechanical signals can be performed. More preferably, the biomechanical signals can enable more data efficient representation of biomechanical actions over the raw accelerometer data.

Accelerometer data can require high frequencies and measurements for multiple axes. The activity monitoring system will generally be operating under battery power, and from design objectives be a small device. Accordingly, wireless communication can be power consuming and slow. The higher level representation of actions provided by the biomechanical signals can enable more efficient wireless communication. Additionally, in some variations, applying the set of biomechanical signals comprises, at the activity monitoring system, intelligent activation of the activity monitoring device and can be used to conserve battery life. For example, periodic sampling of biomechanical signals can be performed in between periods of operating in a low energy mode. When done over a long activity such as an ultra-marathon, biomechanical signals can be monitored over the duration of the race.

Figure 15:
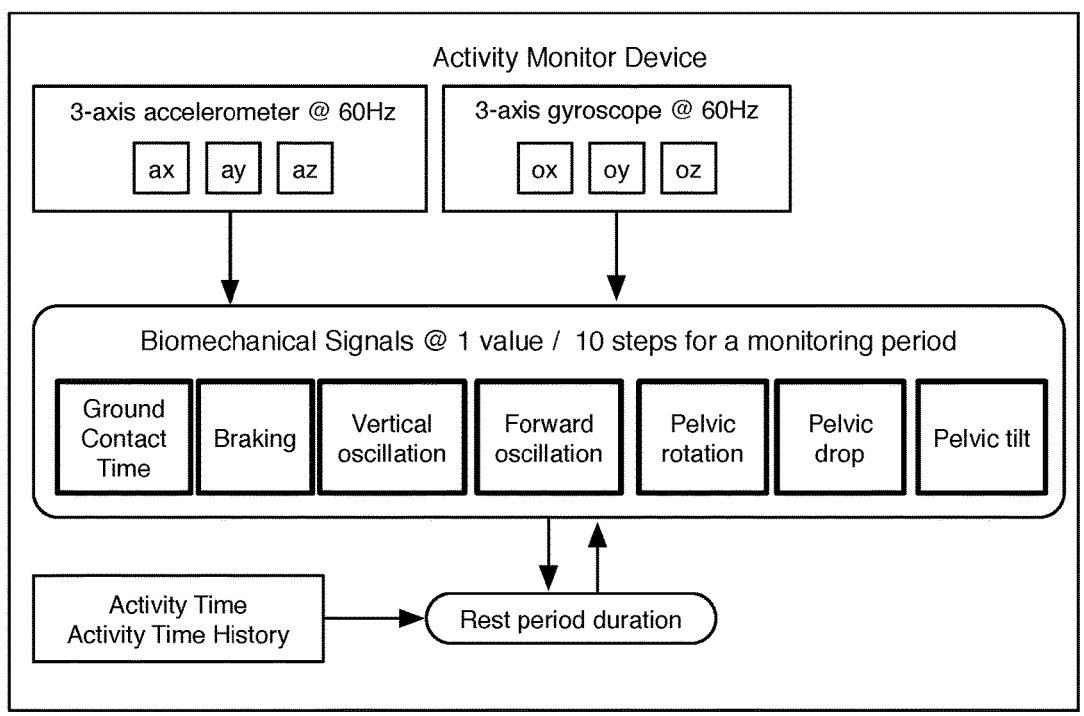

The calculation of biomechanical signals on the sensor device may additionally be adjusted for power, data storage, and/or communication control within the activity monitoring device. Windowing data and/or timing of when biomechanical signals are collected may be done based on battery life of the activity monitoring system, the consistency of the user over multiple sessions (e.g., biomechanical signals may have a low variance), the distance of the run, or any suitable factor. In one variation, biomechanical signals are collected over a sustained duration averaging over biomechanical signals over a number of steps and then deactivated for a designated rest period. The rest period may be activated and the durations set according to various outside factors relating to the activity or performance as shown in FIG. 15. In one variation, the number of segments in a window is dynamically set according to an outside factor. The outside factor can be current run distance, expected run distance, the location of the run (which may be mapped to typical run distances for that user), amount of time running, performance of the user, or any suitable factor. For example, if a user is running an ultra-marathon, the resolution of a biomechanical signal can be averaged over multiple steps, but a user running a 100 meter sprint may want biomechanical signal resolution for each step or even sub-step. Similarly, the communication frequency or time may be adjusted based on similar outside factors. In one variation, communication with an outside device may be initiated only when the biomechanical signals satisfies some condition. For example, when training for a particular target biomechanical signal goal, a user application may communicate the goal value to the activity monitoring system, and communication is only initiated when the user satisfies the goal for some time period or is on track to not meet the goal.

In addition to communicating with an outside computing device, the biomechanical signals can enhance communication between multiple sensor devices of the activity monitoring system. The communication and power approaches of a single sensing device activity monitoring system can additionally be applied to improve communication between two sensor devices. Rather than communicating raw kinematic data, biomechanical signals may be communicated between devices. In one variation, a first subset of biomechanical signals may be calculated on one sensor device and a second subset of biomechanical signals may be calculated on a second sensor device. One biomechanical signal may be communicated to the other sensor device to enable the generation of a second biomechanical signal. For example, step segmentation may be communicated from one sensor device to a second sensor device to enable the generation of a biomechanical signal.

In one variation, applying the set of biomechanical signals can include generating user feedback according to the detected biomechanical signals during the activity session. The feedback can be haptic feedback, visual feedback, auditory feedback, or any suitable medium of delivering feedback to a user.

Figure 16:
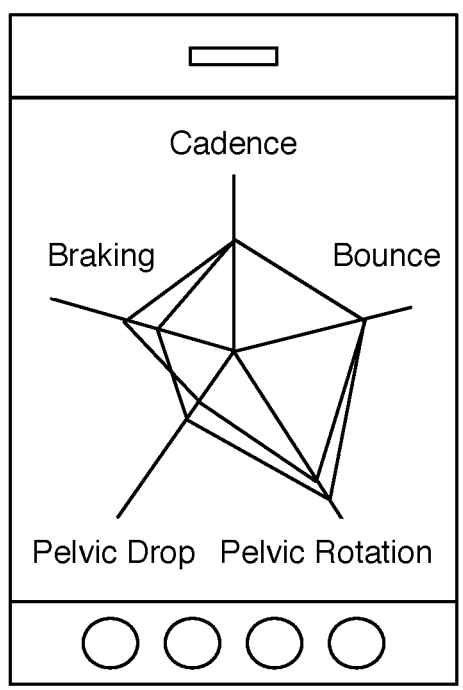
FIG. 16 is a screenshot representation of presenting the biomechanical signals as a graphical representation.

In one variation, applying the biomechanical signals for user feedback can include transforming the signals into an alternative form such as a graphical representation. As shown in FIG. 16, the biomechanical signals can be converted into a graphic that represents a holistic characterization of how a participant moves during an activity. The graphic can additionally reflect changes in biomechanical performance during an activity.

In one variation, block S140 can additionally or alternatively include executing a biomechanical logic model. A biomechanical logic model can analyze and execute any application logic driven by the biomechanical signals. A biomechanical logic model can be used to provide on-demand coaching during a run, provide training advice, generate activity performance reports, or perform any suitable task. The biomechanical logic model can be used to direct user feedback.

In another variation, block S140 can additionally or alternatively include synchronizing the set of biomechanical signals to a second activity stream. The second activity stream is preferably a time-based measurement at least partially overlapping with the time of the biomechanical signals. The biomechanical signals are preferably time synchronized so that a biomechanical signal value at a first instance corresponds to a value of the second activity stream at the first instance. In one variation, the secondary activity stream can be a biosignal of the participant such as heart rate, brain activity, or any suitable measured biological signal. For example, a secondary heart rate monitor can capture heart rate. Alternatively, a monitor device can include the inertial measuring system and a biological sensing system. In another version, the secondary activity stream can be a data stream of one or more external sensors. External sensors are preferably sensors not in contact with the participant. In one exemplary implementation, the external sensors can be sensors on components of a bike that are used to correlate the biological signals to aspects such as wheel speed, pedal forces, bike-tilt, and other suitable aspects. For example, a GPS signal can be used in obtaining a reliable velocity measurement from which a stride length may be calculated. The sensors can be monitoring the user, equipment of the user, the environment of the activity, or any suitable aspect. In one variation, the external sensor can be a camera, which functions to allow a visual capture of an activity to be mapped to the biological signals. Synchronizing the biological signals with the second activity stream may be used in producing an output. For example, a user interface may be used to explore an interactive infographic relating the set of biological signals to the second activity stream. In another variation, the second activity stream can be used in refining, updating, or otherwise modifying the biological signal.

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for personal activity monitoring comprising:
    collecting a set of kinematic data streams from an activity tracking system with at least one activity monitoring system that is attached to a user;
    segmenting at least a subset of the kinematic data streams into a set of segments according to actions of the user;
    generating a set of biomechanical signals from the kinematic data streams wherein a biomechanical signal is a time series signal with values that characterize a biomechanical property during a segment, wherein generating the set of biomechanical signals comprises:
        generating a first integration data set through data integration and baseline error correction across the set of segments of the kinematic data stream, and
        determining at least a first biomechanical signal that is at least partially based on the first integration data set; and
        applying the set of biomechanical signals, wherein applying the set of biomechanical signals comprises, at the activity monitoring system, averaging the biomechanical signal values over a window of consecutive segments, wherein a rest period of the activity monitoring device is dynamically set according to a time duration of the activity or the consistency of the biomechanical signals.

2. The method of claim 1, wherein the activity monitoring system is a single activity monitoring device.

3. The method of claim 1, wherein the activity monitor system is a set of sensor devices that are each attached at distinct points on the user.

4. The method of claim 1, wherein segmenting at least a subset of the kinematic data streams into a set of segments is step segmentation that comprises identifying segmentation points through local extrema in a summation of accelerometer data.

5. The method of claim 4, further comprising adapting orientation of kinematic data streams to a participant orientation, which comprises orienting pitch and roll orientation and determining a forward-backward orientation.

6. The method of claim 1, wherein the set of biomechanical signals comprises ground contact time, braking, pelvic rotation, pelvic tilt, pelvic drop, vertical oscillation of the pelvis, forward velocity properties of the pelvis, and left-right detection.

7. The method of claim 1, wherein generating a first biomechanical signal of the set of biomechanical signals further comprises:
    generating a second integration data set through data integration and baseline error correction across the set of segments of the first integration data set, and
    determining at least a second biomechanical signal that is at least partially based on the second integration data set.

8. The method of claim 1, wherein the first integration data set is generated through data integration of accelerometer data; wherein the first biomechanical signal is a braking biomechanical signal; and further comprising:
    determining a ground contact time signal at least partially based on the first integration data set and the segmentation;
    generating a second integration data set through data integration and baseline error correction across the set of segments of data of the first integration data set, and
    determining a vertical oscillation signal at least partially based on the second integration data set.

9. The method of claim 8, further comprising normalizing the set of kinematic data streams prior to segmenting the kinematic data, which comprises determining a rotational reference of a pelvic region of the participant; and further comprising:
    generating a gyroscopic integration data set through data integration of gyroscopic kinematic data and baseline error correction;
    determining pelvic rotation and pelvic drop signals at least partially based on the gyroscopic integration data set and the rotational reference of the pelvic region.

10. The method of claim 1, wherein segmenting at least a subset of the kinematic data streams into a set of segments is step segmentation; and further comprising classifying segments as left or right steps according to segmented angular velocity gyroscopic data.

11. The method of claim 10, wherein the set of biomechanical signals includes left and right biomechanical signals.

12. The method of claim 1, wherein applying the set of biomechanical signals comprises, at the activity monitoring system, wirelessly communicating a sequence of averaged biomechanical signals to a secondary device.

13. The method of claim 1, wherein applying the set of biomechanical signals comprises generating user feedback according to the detected biomechanical signals during an activity session.

14. A system for tracking activity of a user comprising:
    an activity monitoring device that comprises a housing, an inertial measuring system that collects a set of kinematic data streams, and a signal processor module;
    wherein the activity monitoring device is configured to:
        segment the kinematic data streams into a set of segments according to the steps of the user;
        generate a set of biomechanical signals from the kinematic data streams, wherein a biomechanical signal is a time series signal with values that characterize a biomechanical property during a segment, wherein the activity monitoring device configured to generate the set of biomechanical signals is further configured to:
            generate a first integration data set through data integration and baseline error correction across the set of segments of the set of kinematic data stream;

determine a braking biomechanical signal that is at least partially based on the first integration data set;

determine a ground contact time signal at least partially based on the first integration data set and the segmentation;

generate a second integration data set through data integration and baseline error correction across the set of segments of data of the first integration data set; and determine a vertical oscillation signal at least partially based on the second integration data set; and apply the set of biomechanical signals to an energy conservation scheme that conserves power consumption of the activity monitoring device; and wherein the activity monitoring device is attachable to a user in the pelvic region.

15. The system of claim 14, wherein the set of biomechanical signals comprises ground contact time, braking, pelvic rotation, pelvic tilt, pelvic drop, vertical oscillation of the pelvis, and forward velocity properties of the pelvis.

16. The system of claim 14, wherein the activity monitoring device is configured to segment the kinematic data streams into a set of segments is further configured to classify segments as left or right steps; and wherein the set of biomechanical signals includes left and right biomechanical signals.

17. The system of claim 14, further comprising a user application operable on a computing device that is distinct from the activity monitoring device; and wherein the activity monitoring device is configured to average biomechanical signal values over a window of consecutive segments and communicate the sequence of averaged biomechanical signals to the user application.

* * * * *